US009493519B2

(12) United States Patent
Prescott et al.

(10) Patent No.: US 9,493,519 B2
(45) Date of Patent: Nov. 15, 2016

(54) TOXIN IN TYPE A CLOSTRIDIUM PERFRINGENS

(71) Applicant: University of Guelph, Guelph (CA)

(72) Inventors: John Prescott, Guelph (CA); Iman Mehdizadeh Gohari, Guelph (CA); Valeria Parreira Pinto, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 14/402,956

(22) PCT Filed: May 23, 2013

(86) PCT No.: PCT/CA2013/000503
§ 371 (c)(1),
(2) Date: Nov. 21, 2014

(87) PCT Pub. No.: WO2013/173910
PCT Pub. Date: Nov. 28, 2013

(65) Prior Publication Data
US 2015/0158917 A1 Jun. 11, 2015

Related U.S. Application Data

(60) Provisional application No. 61/650,801, filed on May 23, 2012.

(51) Int. Cl.
| | | |
|---|---|---|
| A61K 39/08 | (2006.01) | |
| C07K 14/33 | (2006.01) | |
| G01N 33/569 | (2006.01) | |
| C07K 16/12 | (2006.01) | |
| C12Q 1/68 | (2006.01) | |
| A61K 39/00 | (2006.01) | |

(52) U.S. Cl.
CPC ............... *C07K 14/33* (2013.01); *A61K 39/08* (2013.01); *C07K 16/1282* (2013.01); *C12Q 1/689* (2013.01); *G01N 33/56911* (2013.01); *A61K 39/00* (2013.01); *A61K 2039/55505* (2013.01); *A61K 2039/55566* (2013.01); *A61K 2039/6068* (2013.01); *C07K 2319/35* (2013.01); *C07K 2319/50* (2013.01); *C12Q 2600/112* (2013.01); *C12Q 2600/158* (2013.01); *G01N 2333/33* (2013.01)

(58) Field of Classification Search
None
See application file for complete search history.

(56) References Cited

U.S. PATENT DOCUMENTS

2016/0052977 A1   2/2016   Prescott et al.

FOREIGN PATENT DOCUMENTS

WO   WO2008148166   * 11/2008

OTHER PUBLICATIONS

Davis et al. Biotechnology and Bioengineering 65(4);382-388, 1999.*
Gohari, Iman Mehdizadeh et al. "A Novel Pore-Forming Toxin in Type A Clostridium perfringens Is Associated with Both Fatal Canine Hemorrhagic Gastroenteritis and Fatal Foal Necrotizing Enterocolitis", PLOS ONE, DOI: 10. 1371, Apr. 8, 2015, pp. 1-27.
Prescott, John et al. "A Novel Pore-Forming Toxin in Type A Clostridium perfringens is Associated with both Fatal Canine Hemorrhagic Gastroenteritis and Fatal Foal Necrotizing Enterocolitis", Abstract, The 3rd Prato Conference on the Pathogenesis of Bacterial Diseases of Animals, https://members.asnevents.com.au/event/1305/abstract/view/19896, Oct. 2014.
"A novel pore-forming toxin in Type A Clostridium perfringens is associated with fatal canine hemorrhagic gastroenteritis and fatal foal necrotizing enterocolitis", Powerpoint, The 3rd Prato Conference on the Pathogenesis of Bacterial Diseases of Animals, Oct. 9, 2014.
Keyburn, A. et al. NetB, a New Toxin That is Associated with Avian Necrotic Enteritis Caused by Clostridium Perfringens. PLoS Pathogens. Feb. 8, 2008, vol. 4, No. 2, pp. e26, ISSN 1553-7366.
Database GENBANK [Mar. 30, 2009], retreived on Jul. 9, 2013. Retrieved from NCBI (National Center for Biotechnology Information). Accession No. EU143239.
Database GENBANK [Mar. 30, 2009], retreived on Jul. 10, 2013. Retrieved from NCBI (National Center for Biotechnology Information). Accession No. ABW71134.
Gohari, Iman Mehdizadeh, Clostridium Perfringens and its Potential Role in Equine Colitis. Guelph Ontario, Canada. Mar. 2012. Master of Science Thesis.
Gohari, Iman Mehdizadeh, Clostridium Perfringens and its Potential Role in Equine Colitis. Guelph Ontario, Canada. Apr. 19, 2012. Presentation of Master of Science Thesis.
Yan, Xu-Xia et al. Structural and Functional Analysis of the Pore-Forming Toxin NetB from Clostridium Perfringens. mBio, Jan./Feb. 2013, vol. 4, Issue 1, pp. 1-9.
Lepp, D. et al., "Identification of Novel Pathogenicity Loci in Clostridium perfringens Strains That Cause Avian Necrotic Enteritis", PLoS ONE, May 2010, vol. 5, No. 5, e10795, pp. 1-18.
Parreira, V.R. et al., "Sequence of Two Plasmids from Clostridium perfringens Chicken Necrotic Enteritis Isolates and Comparison with C. perfringens Conjugative Plasmids", PLoS ONE, Nov. 2012, vol. 7, No. 11, e49753, pp. 1-11.
Miyamoto, K. et al., "Complete Sequencing and Diversity Analysis of the Enterotoxin-Encoding Plasmids in Clostridium pergringens Type A Non-Food-Borne Human Gastrointestinal Disease Isolates", Journal of Bacteriology, Feb. 2006, vol. 188, No. 4, pp. 1585-1598.
Miyamoto, K. et al., "Sequencing and Diversity Analyses Reveal Extensive Similarities between Some Epsilon-Toxin-Encoding Plasmids and the pCPF5603 Clostridium perfringens Enterotoxin Plasmid", Journal of Bacteriology, Nov. 2008, vol. 190, No. 21, pp. 7178-7188.

* cited by examiner

*Primary Examiner* — Oluwatosin Ogunbiyi
(74) *Attorney, Agent, or Firm* — Bereskin & Parr LLP; Melanie Szweras

(57) ABSTRACT

The present disclosure relates to a novel toxin of Type A *C. perfringens* and immunogenic compositions and vaccines thereof. The present disclosure further relates to methods and uses of treating or preventing enteric disease and assays for diagnosing enteric disease in mammals.

10 Claims, 16 Drawing Sheets

NetE x NetB

Identities: 253/322 (79%), Positives: 289/322 (90%), Gaps: 0/322 (0%)

```
NetE  1    MSTSLALASIVSTSIFSTQTQVFASELGNTKKIELKNQNGEIIKEDGKEAIKYTSIDTSS  60
             +S +L L S++STS+FSTQTQVFASEL +  KIELKN +GEIIKE+GKEAIKYTS DT+S
NetB  7    ISITLVLTSVISTSLFSTQTQVFASELNDINKIELKNLSGEIIKENGKEAIKYTSSDTAS  66

NetE  61   CKGLKATLSGTFVEDQYSDKKTALLNLDGFIPSGKKVSGSTYYGKMKWPEVYRISIESAD  120
             KG KATLSGTF+ED +SDKKTALLNL+GFIPS K++ GS YYGKMKWPE YRI+++SAD
NetB  67   HKGWKATLSGTFIEDPHSDKKTALLNLEGFIPSDKQIFGSKYYGKMKWPETYRINVKSAD  126

NetE  121  TANKVKIANSIPKNTIDKKEVSNSIGYSIGGNISVEGKSGSAGINASYSVQNTISYEQPD  180
              N +KIANSIPKNTIDKK+VSNSIGYSIGGNISVEGK+  AGINASY+VQNTISYEQPD
NetB  127  VNNNIKIANSIPKNTIDKKDVSNSIGYSIGGNISVEGKTAGAGINASYNVQNTISYEQPD  186

NetE  181  FRTIQRKDEEKLASWDIKFVETKDGYNLDSYHGIYGNQLFMKSRLYNNGYENFTDDRDLS  240
            FRTIQRKD+  LASWDIKFVETKDGYN+DSYH IYGNQLFMKSRLYNNG +NFTDDRDLS
NetB  187  FRTIQRKDDANLASWDIKFVETKDGYNIDSYHAIYGNQLFMKSRLYNNGDKNFTDDRDLS  246

NetE  241  TLISGGFSPNMAVALTAPKDAKESMITVTYKRFDDEYTLNWETTQWRGSNKRSTACEYTE  300
            TLISGGFSPNMA+ALTAPK+AKES+I V Y+RFD++Y LNWETTQWRG+NK S+  EY E
NetB  247  TLISGGFSPNMALALTAPKNAKESVIIVEYQRFDNDYILNWETTQWRGTNKLSSTSEYNE  306

NetE  301  FMFKINWENHTIERFL  316
            FMFKINW++H IE +L
NetB  307  FMFKINWQDHKIEYYL  322
```

TOXIN IN TYPE A *CLOSTRIDIUM PERFRINGENS*

RELATED APPLICATIONS

This application is a national phase entry of PCT/CA2013/000503 filed May 23, 2013 (which designates the U.S.) which claims priority from U.S. provisional application No. 61/650,801 filed on May 23, 2012, all of which are incorporated herein by reference in their entirety.

INCORPORATION OF SEQUENCE LISTING

A computer readable form of the Sequence Listing "6580-P41878US01_SequenceListing.txt" (29,513 bytes), submitted via EFS-WEB and created on Nov. 18, 2014, is herein incorporated by reference.

FIELD OF THE INVENTION

The present disclosure relates to a novel *Clostridium perfringens* toxin, nucleic acids, proteins and antibodies thereof as well as compositions, methods, uses and screening assays thereof.

BACKGROUND OF THE INVENTION

*Clostridium perfringens* is an anaerobic, ubiquitous bacterium commonly found in soil, water and the intestine of mammals and birds. It is likely the best-known and most common anaerobic pathogen throughout the world (Songer, 1996).

*Clostridium perfringens* was first identified as a cause of human food poisoning-associated enteritis in the 1940s (McClung, 1945). Later, *C. perfringens* infection associated with enteritis necroticans was recognized after World War II in Germany. Various different strains of *C. perfringens* have been shown to cause significant diseases in domestic animals, particularly in food animals (Songer, 1996). These diseases include enteric syndromes such as avian necrotic enteritis, lamb dysentery, neonatal haemorrhagic or necrotizing enteritis in calves, foals and piglets, and ovine, caprine and bovine enterotoxemia. Type A *C. perfringens* has been associated with hemorrhagic gastroenteritis in dogs, as well as severe hemorrhagic and necrotizing enteritis in other animal species (Songer, 1996).

*Clostridium perfringens* as an Enteric Pathogen

*Clostridium perfringens* can produce both major and minor toxins. The pathogenesis of *C. perfringens* enteric diseases is directly associated with the toxins and enzymes that it produces. *Clostridium perfringens* strains are currently classified into five toxinotypes (types A-E) based on the major toxin production profile. The recent discoveries of new toxins in Type A *C. perfringens*, notably NetB and TpeL, as well as the association of the CPE enterotoxin with specific diseases suggest that further work is required to understand the diversity and variety of enteric disease caused by this bacterium.

NetB is a newly discovered toxin associated with necrotic enteritis of chickens. Studies have shown that this toxin has limited amino acid sequence similarity to the beta toxin in *C. perfringens* and the alpha toxin in *Staphylococcus aureus* (Keyburn et al., 2008). A recent study has shown that netB and 36 additional genes are present on a large plasmid-borne pathogenicity locus (Lepp et al., 2010).

Plasmids are an important way that *C. perfringens* acquires and develops novel toxins and other virulence-associated genes while adapting to different hosts and environments. The extraordinary adaptation of *C. perfringens* as a rapidly multiplying "flesh-eater" means that it commonly uses necrotizing toxins as an essential part of its virulence, and these are plasmid-based. Characterizing the plasmids from serious but poorly characterized type A infections in animals is a key to understanding the basis of virulence, and is required for development of control measures (Lepp et al. 2010; Parreira et al. 2012).

*Clostridium perfringens* and Severe Enterocolitis of Foals and Adult Horses

Typhlocolitis (inflammation of the caecum and colon) is an acute and severe disease of horses associated with high mortality, despite therapeutic interventions. Although progress has been made in identifying the causes of acute typhlocolitis in horses, some 60% of cases in horses have no known cause (Ruby et al., 2009; Mehdizadeh et al. 2013).

A number of authors have investigated the role of *C. perfringens* including *Clostridium perfringens* enterotoxin (CPE) in foals, since mild or moderate diarrhea is quite common in these animals. In 1990, Kanoe and colleagues isolated *C. perfringens* from all of the foals with enteric disease as well as in 13.8% of healthy foals; 55% of foals with enteric disease were positive for CPE. Netherwood and others (1996) also found that *C. perfringens* was significantly associated with foal diarrhea.

There is considerable work done on the role of type C *C. perfringens* in neonatal enterocolitis of foals (Traub-Dargatz and Jones, 1993; East et al., 1998; East et al. 2000; Diab et al. 2012), since it is associated with high mortality. Haemorrhagic, necrotizing enteritis of foals has also been described associated with type A *C. perfringens*, and has many similarities clinically or pathologically to type C associated infection (East et al. 1998; Timoney et al., 2005; Hazlett et al., 2011; Potter, 2011). In foals, the disease associated with both type A and type C *C. perfringens* is characteristically a necrotizing infection of the small intestine, particularly of the jejunum. The type A isolates usually possess the cpb2 and cpe genes. The basis of necrotizing enteritis associated with type A *C. perfringens* in foals is not understood, but it is a significant problem in foal rearing such that immunization of mares with *C. perfringens* culture supernatants containing the CPB2 toxin to try to prevent it through lactogenic immunity is sometimes practiced (Timoney et al., 2005). This commonly fatal type A *C. perfringens*-associated disease of foals is present in Ontario (Hazlett et al. 2011).

*Clostridium perfringens* and Canine Hemorrhagic Gastroenteritis

*Clostridium perfringens* type A-associated diarrhea and enteric disease in dogs is not well characterized, but may range in severity from mild and self-limiting to fatal acute hemorrhagic diarrhea (Marks, 2012). Understanding of the role of *C. perfringens* in diarrheal illness in dogs is incomplete, and the spectrum of disease attributed to the organism varies greatly. Its significance as a cause of diarrhea in dogs has been described as "controversial" (Gobeli et al., 2012). There has been an association of diarrheal illness with expression of the cpe enterotoxin gene, although the gene itself may be found in up to 14% of isolates of *C. perfringens* from healthy dogs (Marks, 2012). No gold standard exists for diagnosis (Marks, 2012). Hemorrhagic gastroenteritis is a syndrome characterized by sudden onset of vomiting with production of profuse bloody diarrhea, and is observed especially in small house dogs aged between 2 and 4 years (Marks, 2012). Its pathogenesis is unknown but has been attributed to *C. perfringens* enterotoxin (cpe) production (Marks, 2012). Hemorrhagic gastroenteritis associated with *C. perfringens* type A infection in dogs is characterized by the severe inflammation of the gastrointestinal tract, hemorrhage and rapid death (Prescott et al., 1978; Sasaki et al., 1999; Schelegel et al., 2012a). The presence of large numbers of clostridia-like bacilli, identified as *C. perfringens*, adhering to mucosal surfaces is a striking finding common in cases of fatal hemorrhagic gastroenteritis. Anecdotally, acute canine hemorrhagic gastroenteritis is a syndrome that is commonly recognized by veterinarians in small breed dogs and that may respond to rapid institution of antimicrobial and supportive treatments.

Type A *C. perfringens* has also been associated with gas gangrene and gastrointestinal diseases in humans; and enterotoxemia in cattle and lambs (Songer, 1996).

SUMMARY OF THE INVENTION

The present inventors have isolated a gene encoding a novel toxin produced by Type A *Clostridium perfringens* that likely contributes to necrotizing enteritis/haemorrhagic gastroenteritis in dogs and in foals, and likely in adult horses and in other species, including birds.

Accordingly, the present disclosure provides an isolated nucleic acid molecule comprising a nucleic acid sequence as shown in SEQ ID NO:1 or a variant thereof. Also provided herein is a recombinant expression vector comprising any of the isolated nucleic acid molecules disclosed herein.

In another embodiment, the present disclosure provides an isolated polypeptide encoded by the nucleic acid as shown in SEQ ID NO:1 or a variant thereof. In yet another embodiment, the present disclosure provides an isolated polypeptide having the amino acid sequence as shown in SEQ ID NO:2 or a variant thereof.

In one embodiment, the isolated polypeptide is toxoided.

In another embodiment, the disclosure provides a fusion protein comprising the isolated polypeptide disclosed herein fused to a solubility protein. In one embodiment, the solubility protein is NusA. In a particular embodiment, the fusion protein comprises the amino acid sequence as shown in SEQ ID NO:5 or a variant thereof or is encoded by the nucleic acid sequence as shown in SEQ ID NO:24 or a variant thereof.

Further provided is a host cell comprising any of the isolated nucleic acid molecules disclosed herein, any of the recombinant expression vectors disclosed herein, or any of the isolated polypeptides or fusion proteins disclosed herein.

In yet another embodiment, the disclosure provides a binding protein that binds any of the isolated polypeptides disclosed herein. In one embodiment, the binding protein is an antibody or antibody fragment. In an embodiment, the antibody is a monoclonal antibody.

Also provided herein is an immunogenic composition comprising any of the isolated polypeptides disclosed herein, any of the fusion proteins disclosed herein or any of the host cells disclosed herein; and a pharmaceutically acceptable carrier.

Further provided herein is an immunogenic composition comprising supernatant isolated from a NetE-positive *C. perfringens* strain. In one embodiment, the supernatant is concentrated. In another embodiment, the immunogenic composition comprising supernatant further comprises additional isolated NetE protein or NetE-solubility fusion protein.

In one embodiment, the immunogenic composition further comprises an adjuvant.

In another embodiment, the immunogenic composition disclosed herein further comprising an additional *C. perfringens* toxin protein, optionally Cpe, Cpa, NetB, Cpb2 or TpeL. In one embodiment, the additional *C. perfringens* toxin protein is Cpe.

Also provided herein are methods and uses of any of the immunogenic compositions and binding proteins disclosed herein. In one embodiment, the present disclosure provides a method of treating or preventing Type A *C. perfringens* enteric disease comprising administering an immunogenic composition or binding protein disclosed herein to a subject in need thereof. Also provided herein is a use of an immunogenic composition or binding protein disclosed herein for treating or preventing Type A *C. perfringens* enteric disease in a subject in need thereof. Further provided is an immunogenic composition or binding protein disclosed herein for use in treating or preventing Type A *C. perfringens* enteric disease in a subject in need thereof. Even further provided is use of an immunogenic composition or binding protein disclosed herein in the preparation of a medicament for treating or preventing Type A *C. perfringens* enteric disease in a subject in need thereof.

In one embodiment, the subject is a mammal or bird. In a particular embodiment, the subject is a horse, dog or human. In another embodiment, the enteric disease is haemorrhagic or necrotizing gastroenteritis. In yet another embodiment, the enteric disease is haemorrhagic or necrotizing small intestinal enteritis. In a further embodiment, the enteric disease is typhlocolitis.

Further provided herein is a method of monitoring or diagnosing enteric disease in a subject, comprising the steps of:

a) detecting the presence of NetE of *Clostridium perfringens* in a sample from the subject; and b) comparing the expression of the NetE from the sample with a control;

wherein a difference in expression of NetE in the sample from the subject as compared to the control is indicative of enteric disease in the subject.

In one embodiment, the NetE comprises any of the polypeptides disclosed herein or is encoded by any of the nucleic acid molecules disclosed herein.

In an embodiment, the NetE is detected in step (a) by detecting a nucleic acid molecule encoding the toxin in the sample by hybridization using a probe specific for the toxin or by PCR using primers specific for the toxin, such as the primers as shown in SEQ ID NO:3 and SEQ ID NO:4.

In another embodiment, the NetE is detected in step (a) by detecting a NetE polypeptide using an antibody that specifically binds the NetE. In one embodiment, the antibody is a monoclonal antibody.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which:

FIG. 4 shows the amino acid homology of toxins NetE and NetB (SEQ ID NOs:2 and 23, respectively).

DETAILED DESCRIPTION

Figure 1A:
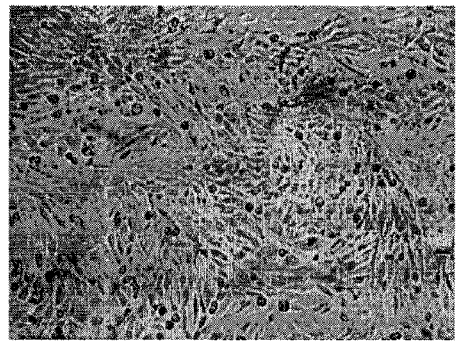
FIG. 1A shows a confluent layer of equine ovarian cell line, with no evidence of toxicity.
Figure 1B:
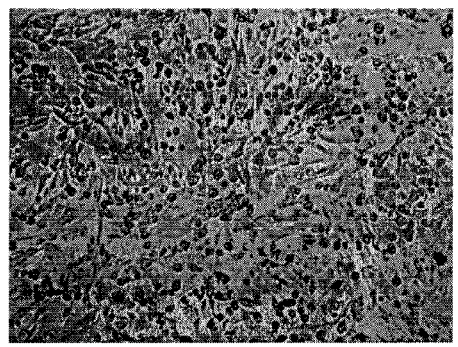
FIG. 1B shows equine ovarian cell line with 1+ toxicity. About 25% of the cells are rounded or detached.
Figure 1C:
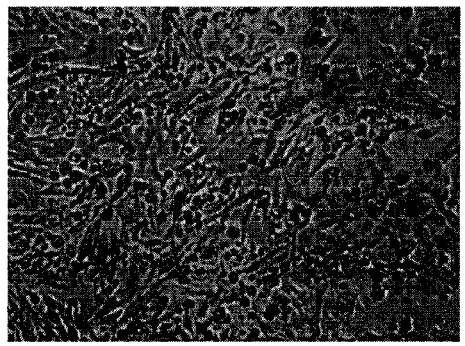
FIG. 1C shows equine ovarian cell line with 2+ toxicity. About 50% of the cells are rounded or detached.
Figure 1D:
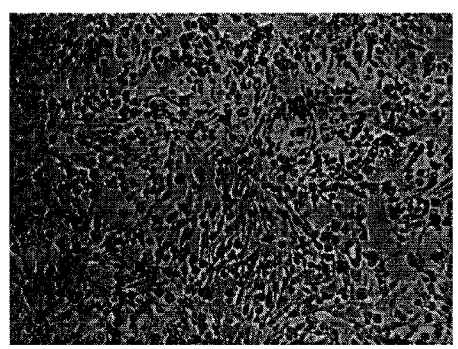
FIG. 1D shows equine ovarian cell line with 3+ toxicity. About 75% of the cells are rounded or detached.
Figure 1E:
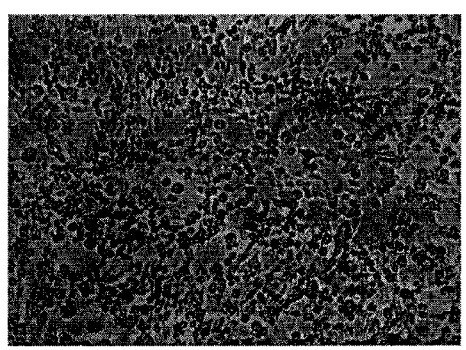
FIG. 1E shows equine ovarian cell line with 4+ toxicity. About 100% of the cells are rounded or detached.

The present inventors isolated a new gene related to a known pore-forming toxin of Clostridium perfringens and purified this novel toxin. Through PCR, this gene was identified in some other type A isolates from foals with fatal necrotizing enteritis, from adult horses with typhlocolitis and from dogs with fatal haemorrhagic enteritis.

NetE (Toxin E) Nucleic Acids and Proteins

Accordingly, the present disclosure provides an isolated nucleic acid molecule comprising a nucleic acid sequence as shown in SEQ ID NO:1 or a variant thereof. In one embodiment, the nucleic acid molecule comprises, consists essentially of or consists of the nucleic acid sequence as shown in SEQ ID NO:1.

The term "isolated" refers to a nucleic acid substantially free of cellular material or culture medium when produced by recombinant DNA techniques, or chemical precursors, or other chemicals when chemically synthesized.

The term "nucleic acid molecule" is intended to include unmodified DNA or RNA or modified DNA or RNA. For example, the nucleic acid molecules or polynucleotides of the disclosure can be composed of single- and double stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The nucleic acid molecules of the disclosure may also contain one or more modified bases or DNA or RNA backbones modified for stability or for other reasons. "Modified" bases include, for example, tritiated bases and unusual bases such as inosine. A variety of modifications can be made to DNA and RNA; thus "nucleic acid molecule" embraces chemically, enzymatically, or metabolically modified forms. The term "polynucleotide" shall have a corresponding meaning.

The term "toxE or toxin E" or "NetE" are synonymous and are used herein to refer to the novel gene or protein disclosed herein isolated from Type A Clostridium perfringens.

Variant nucleic acid sequences include nucleic acid sequences that hybridize to the nucleic acid sequence as shown in SEQ ID NO: 1 (or 24 disclosed herein) under at least moderately stringent hybridization conditions, or have at least 85%, at least 90%, at least 95%, or at least 98% sequence identity to the nucleic acid sequence of SEQ ID NO:1 or 24.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.–16.6 (Log 10 [Na+])+0.41(% (G+C)–600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm—5° C. based on the above equation, followed by a wash of 0.2× SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

Variant nucleic acid sequences or molecules also include analogs of the nucleic acid sequences and molecules described herein. The term "a nucleic acid sequence which is an analog" means a nucleic acid sequence which has been modified as compared to the sequences described herein, wherein the modification does not alter the utility of the sequences described herein. The modified sequence or analog may have improved properties over the sequence shown in SEQ ID NO:1 or 24. One example of a modification to prepare an analog is to replace one of the naturally occurring bases (i.e. adenine, guanine, cytosine or thymidine) of the sequence shown in SEQ ID NO:1 with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID NO:1 or 24. For example, the nucleic acid sequences may contain phosphorothioates, phosphotriesters, methyl phosphonates, and phosphorodithioates.

A further example of an analog of a nucleic acid molecule of the disclosure is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complementary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequences.

The variant nucleic acid sequences further include conservatively substituted nucleic acid sequences. In the context of this specification, the term "conserved" describes similarity between sequences. The degree of conservation between two sequences can be determined by optimally aligning the sequences for comparison. Sequences may be aligned using the Omiga software program, Version 1.13. (Oxford Molecular Group, Inc., Campbell, Calif.). The Omiga software uses the Clustal W Alignment algorithms [Higgins et al., 1989; Higgins et al., 1991; Thompson et al. 1994] Default settings used are as follows: Open gap penalty 10.00; Extend gap penalty 0.05; Delay divergent sequence 40 and Scoring matrix—Gonnet Series. Percent identity or homology between two sequences is determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

Further, it will be appreciated that variants include nucleic acid molecules comprising nucleic acid sequences having substantial sequence homology or identity with the nucleic acid sequence as shown in SEQ ID NO:1 or 24. The term "sequences having substantial sequence homology or identity" means those nucleic acid sequences that have slight or inconsequential sequence variations from these sequences, i.e., the sequences function in substantially the same manner to produce functionally equivalent proteins.

Nucleic acid sequences having substantial homology include nucleic acid sequences having at least about 85 percent identity with a nucleic acid sequence of SEQ ID NO:1 or 24. The level of homology, according to various aspects of the disclosure is at least about 90 percent; at least about 95 percent; or at least about 98 percent. Methods for aligning the sequences to be compared and determining the level of homology between the sequences are described in detail above.

Sequence identity can be calculated according to methods known in the art. Sequence identity is most preferably assessed by the algorithm of BLAST version 2.1 advanced search. BLAST is a series of programs that are available online (see world wide web at ncbi.nlm.nih.gov/BLAST). The advanced blast search (see world wide web at ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schiffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "Power-BLAST: A new network BLAST application for interactive or automated sequence analysis and annotation." Genome Res. 7:649656.

Variants further include nucleic acid sequences which differ from the nucleic acid sequence shown in SEQ ID NO:1 or 24 due to degeneracy in the genetic code. Such nucleic acids encode functionally equivalent proteins but differ in sequence from the above mentioned sequences due to degeneracy in the genetic code.

An isolated nucleic acid molecule of the disclosure which comprises DNA can be isolated by preparing a labelled nucleic acid probe based on all or part of the nucleic acid sequences as shown in SEQ ID NO:1 or 24 and using this labelled nucleic acid probe to screen an appropriate DNA library (e.g. a cDNA or genomic DNA library).

An isolated nucleic acid molecule of the disclosure which is DNA can also be isolated by selectively amplifying the nucleic acid using the polymerase chain reaction (PCR) methods and cDNA or genomic DNA. It is possible to design synthetic oligonucleotide primers from the nucleic acid sequence as shown in SEQ ID NO:1 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294 5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the disclosure which is RNA can be isolated by cloning the cDNA into an appropriate vector which allows for transcription of the cDNA to produce an RNA molecule which encodes NetE or a variant thereof. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the disclosure may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

In another embodiment, the present disclosure provides an isolated polypeptide encoded by the nucleic acid as shown in SEQ ID NO:1 or a variant thereof or an isolated polypeptide having the sequence as shown in SEQ ID NO:2 or a variant thereof.

In one embodiment, the isolated polypeptide comprises, consists essentially of or consists of SEQ ID NO:2.

The term "isolated polypeptide" refers to a polypeptide substantially free of cellular material or culture medium when produced by recombinant DNA techniques, or chemical precursors or other chemicals when chemically synthesized.

In one embodiment, the isolated polypeptide is toxoided.

The term "toxoided" refers to inactivating the toxicity of the polypeptide. Approaches to toxoiding are known in the art and include, without limitation, inactivation with formalin in the procedure outlined by Ito, A. 1968. Alpha-toxoid of *Clostridium perfringens*. I. Purification and toxoiding of alpha-toxin of *C. perfringens*. Jpn. J. Med. Sci. Biol. 21:379-391. An alternative approach is a genetic approach to toxoiding similar to that described by Yan X-X, Porter C C, Hardy S, Steer D, Smith I A, et al. Structural and functional analysis of the pore-forming toxin NetB from *Clostridium perfringens*. mBio 2013; 4: 1-9. This approach involves using either cytotoxicity or hemolysis as a screen, and then using site directed mutagenesis of NetE to remove the cytotoxic activity of the toxin while retaining its immunogenicity. The formalin inactivation involves progressive treatment of the NetE or rNetE-NusA protein to remove toxicity.

Even further included herein is a fusion protein comprising the NetE protein disclosed herein fused with a solubilizing partner. In one embodiment, the solubility partner is bacterioferritin (BFR) or heat shock protein (GrpE). In another embodiment, the solubilizing partner is NusA. In one embodiment, the NusA-NetE fusion protein comprises the amino acid sequence as shown in SEQ ID NO:5 or a variant thereof. In another embodiment, the NusA-NetE fusion protein is encoded by the nucleic acid sequence as shown in SEQ ID NO:24 or a variant thereof. In a particular embodiment, the fusion protein comprises, consists essentially of or consists of the amino acid sequence as shown in SEQ ID NO:5.

The term "NusA" as used herein refers to the NusA protein from any species or source. In one embodiment, the NusA protein is from *E. coli* and has the GenBank accession number: AAC76203.1 GI:1789560.

A person skilled in the art will appreciate that the disclosure includes variants to the amino acid sequences disclosed herein, including chemical equivalents. Such equivalents include proteins that perform substantially the same function in substantially the same way. For example, equivalents include, without limitation, conservative amino acid substitutions, deletions and insertions.

A "conservative amino acid substitution" as used herein, is one in which one amino acid residue is replaced with another amino acid residue without abolishing the protein's desired properties.

Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology, i.e., sequence similarity, of a variant protein with a naturally occurring protein, the greater the retention of its activity. Of course, as protein variants having the activity of NetE as described herein are intended to be within the scope of this disclosure, so are nucleic acids encoding such variants.

In one embodiment, the variant amino acid sequences have at least 85%, at least 90% or at least 95% identity to the amino acid sequence as shown in SEQ ID NO:2 or 5 or to the amino acid sequence encoded by the nucleic acid sequence as shown in SEQ ID NO:1 or 24.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions·times·100%). In one embodiment, the two sequences are the same length. The determination of percent identity between two sequences can also be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Variants of the NetE gene or protein or fusion protein disclosed herein may be prepared by introducing mutations in the nucleotide sequence encoding the protein. Mutations in nucleotide sequences constructed for expression of analogs of a protein of the disclosure must preserve the reading frame of the coding sequences. Furthermore, the mutations will preferably not create complementary regions that could hybridize to produce secondary mRNA structures, such as loops or hairpins, which could adversely affect translation of the mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et at (Molecular Cloning: A Laboratory Manual, 2nd Ed., Cold Spring Harbor Laboratory Press, 1989).

The proteins described above (including truncations, analogs, etc.) may be prepared using recombinant DNA methods. These proteins may be purified and/or isolated to various degrees using techniques known in the art. Accordingly, nucleic acid molecules of the present disclosure having a sequence which encodes a protein of the disclosure may be incorporated according to procedures known in the art into an appropriate expression vector which ensures good expression of the protein. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the disclosure and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The disclosure therefore contemplates a recombinant expression vector of the disclosure containing a nucleic acid molecule of the disclosure, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The recombinant expression vectors of the disclosure may also contain a selectable marker gene that facilitates the selection of host cells transformed or transfected with a recombinant molecule of the disclosure. Examples of selectable marker genes are genes encoding a protein which confers resistance to certain drugs, such as G418 and hygromycin. Examples of other markers which can be used are: green fluorescent protein (GFP), β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the disclosure and in particular to determine the effect of a mutation on expression and phenotype. It will be appreciated that selectable markers can be introduced on a separate vector from the nucleic acid of interest.

The recombinant expression or cloning vectors of the disclosure may also contain genes which encode a fusion moiety which provides increased expression of the recombinant protein; increased solubility of the recombinant protein, such as NusA described herein; and aid in the purification of a target recombinant protein by acting as a ligand in affinity purification, such as a His-tag. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the disclosure. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium chloride mediated transformation. Nucleic acid can be introduced into mammalian cells via conventional techniques such as calcium phosphate or calcium chloride co precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Accordingly, further provided is a host cell comprising any of the isolated nucleic acid molecules disclosed herein, any of the recombinant expression vectors disclosed herein, or any of the isolated polypeptides or fusion proteins disclosed herein.

Suitable host cells include a wide variety of prokaryotic and eukaryotic host cells. For example, the proteins of the disclosure may be expressed in bacterial cells such as E. coli, insect cells (using baculovirus), yeast cells or mammalian cells, COS1 cells. Other suitable host cells can be found in Goeddel, Gene Expression Technology: Methods in Enzymology 185, Academic Press, San Diego, Calif. (1991).

The disclosure includes a microbial cell that contains and is capable of expressing a heterologous nucleic acid molecule having a nucleotide sequence as encompassed by the disclosure. The heterologous nucleic acid molecule can be DNA.

The disclosure also contemplates a process for producing a NetE toxin protein as defined by the disclosure. The process includes such steps as:

preparing a DNA fragment including a nucleotide sequence which encodes said protein;

incorporating the DNA fragment into an expression vector to obtain a recombinant DNA molecule which includes the DNA fragment and is capable of undergoing replication;

transforming a host cell with said recombinant DNA molecule to produce a transformant which can express said protein;

culturing the transformant to produce said protein; and recovering said protein from resulting cultured mixture.

More particularly, the disclosure provides a method of preparing a purified protein of the disclosure comprising introducing into a host cell a recombinant nucleic acid encoding the protein, allowing the protein to be expressed in the host cell and isolating and purifying the protein. Preferably, the recombinant nucleic acid is a recombinant expression vector. Proteins can be isolated from a host cell expressing the protein and purified according to standard procedures of the art, including ammonium sulfate precipitation, column chromatography (e.g. ion exchange, gel filtration, affinity chromatography, etc.), electrophoresis, and ultimately, crystallization [see generally, "Enzyme Purification and Related Techniques", *Methods in Enzymology*, 22, 233-577 (1971)].

Alternatively, the protein or parts thereof can be prepared by chemical synthesis using techniques well known in the chemistry of proteins such as solid phase synthesis [Merrifield, J. Am. Chem. Assoc. 85:2149-2154 (1964); Frische et al., J. Pept. Sci. 2(4): 212-22 (1996)] or synthesis in homogeneous solution [Houbenweyl, Methods of Organic Chemistry, ed. E. Wansch, Vol. 15 I and II, Thieme, Stuttgart (1987)].

In yet another embodiment, the disclosure provides a binding protein that binds any of the isolated polypeptides disclosed herein.

The term "binding protein" as used herein refers to a protein that specifically binds to another substance. In an embodiment, the binding proteins are antibodies or antibody fragments thereof. In a further embodiment, the binding proteins are monoclonal antibodies or fragments thereof. In one embodiment, the binding protein is an antibody or antibody fragment that binds to a protein having the amino acid sequence of SEQ ID NO:2 or a variant thereof or to a protein encoded by the nucleic acid sequence as shown in SEQ ID NO:1 or a variant thereof.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

Conventional methods can be used to prepare the antibodies. For example, by using a peptide of a protein of the disclosure, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)); the EBV-hybridoma technique to produce human monoclonal antibodies (Cole et al. Monoclonal Antibodies in Cancer Therapy (1985) Allen R. Bliss, Inc., pages 77-96); and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for a protein of the disclosure.

Chimeric antibody derivatives, i.e., antibody molecules that combine a non-human animal variable region and a human constant region are also contemplated within the scope of the disclosure. Chimeric antibody molecules can include, for example, the antigen binding domain from an antibody of a mouse, rat, or other species, with human constant regions. Conventional methods may be used to make chimeric antibodies containing the immunoglobulin variable region which recognizes a NetE protein of the disclosure (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the disclosure as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982); and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments reactive against a protein of the disclosure may also be generated by screening expression libraries encoding immunoglobulin genes, or portions thereof, expressed in bacteria with peptides produced from nucleic acid molecules of the present disclosure. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

The disclosure also contemplates the use of "peptide mimetics" for the binding proteins. Peptide mimetics are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of the binding proteins of the disclosure. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to the binding proteins of the disclosure.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Compositions, Methods and Uses

Further provided herein is a composition comprising a binding protein disclosed herein; and a pharmaceutically acceptable carrier.

Also provided herein is an immunogenic composition comprising any of the isolated polypeptides or fusion proteins disclosed herein or any of the host cells disclosed herein; and a pharmaceutically acceptable carrier.

Even further provided is an immunogenic composition comprising supernatant isolated from a NetE-positive *C. perfringens* strain.

A person skilled in the art would readily be able to determine whether a particular strain for example, from a case of canine haemorrhagic gastroenteritis or of equine severe necrotizing enteritis, particularly in foals, is NetE-positive, for example, by using PCR primers to amplify the NetE nucleic acid sequence or using antibodies that specifically recognize the NetE protein. Methods for testing for NetE are disclosed herein.

Methods for preparing *C. perfringens* supernatants from Net-E positive strains isolated from canine haemorrhagic gastroenteritis or equine severe necrotizing enteritis, particularly of foals, are known in the art and include the method described in the Examples section.

In one embodiment, the immunogenic composition comprises a concentrated supernatant from a NetE-positive *C. perfringens* strain.

The term "concentrated" as used herein refers to increasing the percentage of proteins relative to broth in the supernatant and includes a supernatant that has been concentrated at least 5 times, 10 times, 20 times, 30 times, 50 times, 100 times or more compared to a supernatant without concentration.

The term "immunogenic composition" as used herein refers to a composition that is able to elicit an immune response, including without limitation, production of antibodies or cell mediated immune responses, against an antigen present in the composition.

In one embodiment, the immunogenic composition is a vaccine. The term "vaccine" as used herein refers to an immunogenic composition that is capable of eliciting a prophylactic and/or therapeutic response that prevents, cures or ameliorates disease.

In one embodiment, the immunogenic composition comprises a NetE toxin protein disclosed herein and a NusA-NetE fusion protein disclosed herein, and a pharmaceutically acceptable carrier.

In a further embodiment, the immunogenic composition further comprises an antibiotic or anti-diarrheal medication.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethyl-amino ethanol, histidine, procaine, etc.

In one embodiment, the immunogenic composition further comprises an adjuvant. The term "adjuvant" as used herein refers to a substance that is able to enhance the immunostimulatory effects of the antigen described herein but does not have any specific antigenic effect itself. Typical adjuvants include, without limitation, Freund's complete or incomplete adjuvant, aluminium salts, squalene, oil-based adjuvants, selected toll-like receptor ligands, Ribi's adjuvant, ISCOMs, Keyhole Limpet Hemocyanin (KLH) and others.

In another embodiment, the immunogenic compositions disclosed herein further comprise an additional *C. perfringens* toxin protein. In one embodiment, the additional *C. perfringens* toxin protein is *Clostridium perfringens* enterotoxin (Cpe), *Clostridium perfringens* alpha toxin (Cpa), necrotic enteritis toxin B-like (NetB), beta2 toxin (Cpb2) or Toxin of *Clostridium perfringens* Large (TpeL).

The Cpe, Cpa, NetB, Cpb2 or TpeL can be from any species or source. For example, NetB can be that described in GenBank EU143239, GI:158524053; Cpe can be that described in GenBank M98037.1, GI:144927; Cpb2 can be that described in GenBank AY609161.1, GI:51949825; TpeL can be that described in GenBank EU848493, GI:194338410 and Cpa can be that described in GenBank X17300.1, GI:40619.

Also provided herein are methods and uses of any of the immunogenic compositions or binding proteins disclosed herein. In one embodiment, the present disclosure provides a method of treating or preventing Type A *Clostridium perfringens* enteric disease comprising administering an immunogenic composition or binding protein disclosed herein to a subject in need thereof. Also provided herein is a use of an immunogenic composition or binding protein disclosed herein for treating or preventing Type A *Clostridium perfringens* enteric disease in a subject in need thereof. Further provided is an immunogenic composition or binding protein disclosed herein for use in treating or preventing Type A *Clostridium perfringens* enteric disease in a subject in need thereof. Even further provided is use of an immunogenic composition or binding protein disclosed herein in the preparation of a medicament for treating or preventing Type A *Clostridium perfringens* enteric disease in a subject in need thereof.

"Type A *Clostridium perfringens* enteric disease" as used herein refers to a disease of the intestine caused by type A *Clostridium perfringens* infection and includes, without limitation, a serious *Clostridium perfringens* toxin-induced inflammation of the intestine associated with death (necrosis) of intestinal mucosal lining cells, and in cells underneath the mucosa, with inflammation in these structures sometimes marked by haemorrhage, and with serious impairment of intestinal function that may lead to death.

Accordingly, in another embodiment, the enteric disease is haemorrhagic or necrotizing gastroenteritis. In yet another embodiment, the enteric disease is haemorrhagic or necrotizing small intestinal enteritis. In a further embodiment, the enteric disease is typhlocolitis.

The term "administering a protein" includes both the administration of the protein as well as the administration of a nucleic acid sequence encoding the protein to an animal or to a cell in vitro or in vivo. The term "administering" also includes the administration of a cell that expresses the protein.

The term "treating" or "treatment" as used herein means administering to a subject a therapeutically effective amount of the compositions of the present disclosure and may consist of a single administration, or alternatively comprise a series of applications.

As used herein, and as well understood in the art, "treatment" or "treating" is also an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, spread of disease, delay or slowing of disease progression, amelioration or palliation of the disease state, and remission (whether partial or total), whether detectable or undetectable. "Treatment" can also mean prolonging survival as compared to expected survival if not receiving treatment. Further any of the treatment methods or uses described herein can be formulated alone or for contemporaneous administration with other agents or therapies. "Treatment" or "treating" can also include preventing the onset of disease.

The term "subject" or "animal" as used herein includes all members of the animal kingdom including birds and mammals, such as humans (patients), horses, lambs, dogs, black-footed ferrets, mice, minks, muskrats, camels, birds and rabbits. In one embodiment, the subject is a mammal such as a horse, lamb, dog, or human.

In accordance with the methods disclosed herein, the compositions disclosed herein may be administered to a patient in a variety of forms depending on the selected route of administration, as will be understood by those skilled in the art. For example, the compositions may be administered by oral or parenteral administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration.

The current treatment for enteric disease is almost exclusively antibiotics but it could include anti-diarrheal medications. Accordingly, in another embodiment, the methods and uses include co-administration with antibiotics or anti-diarrheal medications.

The term "co-administering" as used herein means that the immunogenic compositions and the current treatment is administered contemporaneously. The term "contemporaneous administration" of two substances to an individual means providing each of the two substances so that they are both biologically active in the individual at the same time. The exact details of the administration will depend on the pharmacokinetics of the two substances in the presence of each other. In one embodiment, the immunogenic composition is administered prior to the current treatment. In another embodiment, the immunogenic composition is administered at the same time as the current treatment. In yet another embodiment, the immunogenic composition is administered after the current treatment.

The dosage of the compositions disclosed herein can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compositions may be administered initially in a suitable dosage that may be adjusted as required, depending on the clinical response.

Diagnostic Methods

Further provided herein is a method of monitoring or diagnosing enteric disease in a subject, comprising the steps of:

a) detecting the presence of NetE toxin of *Clostridium perfringens* in a sample from the subject; and b) comparing the expression of the NetE toxin from the sample with a control;

wherein a difference in expression of NetE toxin in the sample from the subject as compared to the control is indicative of enteric disease in the subject.

In one embodiment, the NetE toxin comprises any of the polypeptides disclosed herein or is encoded by any of the nucleic acid molecules disclosed herein.

In another embodiment, the method further comprising obtaining a sample from a subject prior to (a).

In an embodiment, the Net E toxin is detected in step (a) by detecting a nucleic acid molecule encoding the toxin in the sample by hybridization using a probe specific for the toxin or by PCR using primers specific for the toxin, such as the sequences shown in SEQ ID NO:3 and SEQ ID NO:4.

In another embodiment, the NetE is detected in step (a) by detecting a NetE polypeptide using an antibody that specifically binds the NetE. In one embodiment, the antibody is a polyclonal antibody. In another embodiment, the antibody is a monoclonal antibody.

The term "control" as used herein refers to a sample from a subject or a group of subjects, which do not have enteric disease. The control can also be a predetermined standard.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Materials and Methods

*Clostridium perfringens* Strain Collection, Growth Media, and Detection of Toxin Genes Strain Collection:

The strain collection of *C. perfringens* in the Department of Pathobiology, University of Guelph, includes isolates from about 950 different animals, as well as about 45 type strains, largely with American Type Culture Collection (ATCC) or National Collection of Type Cultures (NCTC)

designations, among other sources. The 950 individual animal isolates are predominantly from the feces of diarrheic or healthy cattle, chickens, dogs, pigs or horses, collected for different purposes, largely since 2008. Some isolates come from cases of fatal enteric or diarrheal disease in animals presented to the Animal Health Laboratory, University of Guelph, some of which have detailed pathological diagnostic descriptions associated with them. In addition, some isolates have been imported because they have specific diagnoses attached to them; these include type A isolates from fatal necrotizing enteritis in foals or fatal canine hemorrhagic enteritis (Dr T. Besser, Washington State University, Pullman, Wash., USA) or originated from diarrheal illness in dogs (Dr R. J. Carman, TechLabs, Blacksburg, Va.; Dr V. Perreten, Institute of Veterinary Bacteriology, University of Bern, Switzerland). Many of the isolates have been genotyped using a real-time PCR genotyping approach, as part of several publications from the Department of Pathobiology characterizing the possible association of these isolates with various diseases in different species (Nowell et al., 2010; Chan et al., 2012; Farzan et al., 2012; Kircanski et al., 2012a; Schlegel et al., 2012b; Mehdizadeh et al., 2013).

Growth Media:

Each isolate selected from the strain collection was grown overnight at 37° C. under anaerobic conditions (80% $N_2$, 10% $H_2$, 10% $CO_2$) on TPG medium (5% Tryptone [Becton, Dickinson and Company, Sparks, Md.], 0.5% Proteose peptone [Fisher Scientific, ON], 0.4% Glucose, and 0.1% Thioglycolic acid [Sigma-Aldrich, St. Louis, Mo.]). All *C. perfringens* isolates were also cultivated in blood agar (Trypticase Soy Agar [Fisher] with 5% sheep blood) plates aerobically to confirm purity. *E. coli* strains were grown on Luria-Bertani (LB) agar plates (Difco Laboratories, Detroit, Mich.) at 37° C. in aerobic conditions.

Presence of Toxin Genes:

Genomic DNA was isolated from 5 ml of overnight culture in Brain Heart Infusion (BHI) broth (Difco) at 37° C. under anaerobic conditions (Pospiech and Neumann, 1995). After precipitation, DNA pellets were washed twice with 70% ethanol and resuspended in TE buffer (10 mM Tris-Cl, pH 7.5, 1 mM EDTA). Detection of various toxin genes was carried out by PCR amplification of each *C. perfringens* isolate. The presence of the netE toxin gene (also termed toxin E gene) was detected by PCR amplification of an internal fragment, using primers designed from the *C. perfringens* plasmid sequence (pNetE_JP728) described herein. PCR-based toxin typing of alpha toxin (cpa), beta-2 toxin gene (cpb2) and the enterotoxin gene (cpe) was also done. All primers used are described in Table 1. Amplifications were performed in a 25 μl total volume containing the following: 5 μl of template DNA, 1×PCR buffer with $Mg^{+2}$ (New England BioLabs, Pickering, ON), 0.2 mM deoxynucleoside triphosphate mixture, 2.5 units of TaqDNA polymerase (New England BioLabs), and 800 nM of each primer. A touchdown PCR program was used: 94° C. for 3 min, 35 cycles of 94° C. for 15 sec, 65° C. to 50° C. for 15 sec/cycle (the annealing temperature is decreased by 1° C. every cycle until 50° C.), extension at 68° C. for 5 min, and finally, 68° C. for 10 min. PCR product sizes were determined by agarose gel electrophoresis and visualized by ethidium bromide staining and photographed under UV light.

Plasmid DNA Isolation and Southern Characterization of netE Gene Location

Plasmid DNA was purified using midi-Qiagen columns (Qiagen, ON) following the manufacturer's instructions.

Plasmids Sequencing:

The partial nucleotide sequence of plasmids from *C. perfringens* strain JP728 was determined using the 454 GS Junior Titanium platform (Roche Applied Science, Laval, QC). In brief, plasmid DNA 10 μg was nebulized at 45 psi for 1 min to shear the DNA into fragments smaller than 400 bp. Sheared DNA was end repaired by incubating with 15 U of T4 polynucleotide kinase and 15 U of T4 DNA polymerase in the presence of buffer and a dNTP mix (10 mM each) at 12° C. for 15 min and 25° C. for 15 min. DNA was then purified by MinElute PCR Purification Kit (Qiagen). The 454-sequencing adaptors were ligated to the DNA fragments according to the GS Junior Titanium shotgun DNA Library Preparation Method (Roche Applied Science) by incubating with 104 U of ligase in the presence of ligase buffer at 25° C. for 15 min. The reaction was purified by MinElute PCR Purification Kit (Qiagen). The nucleotide sequence reads obtained were assembled using the Newbler (version 2.5p1) de novo sequence assembly software (Roche Applied Science).

Plasmid Sequencing and Annotation:

Partial sequences were automatically annotated by Rapid Annotation using Subsystem Technology (RAST). BLASTN and BLASTX analyses were performed to compare the established sequences to known *C. perfringens* plasmids in the NCBI database.

Plasmid Pulse Field Gel Electrophoresis:

PFGE was performed to analyze the presence of plasmids in total of 12 *C. perfringens* isolates (6 canine and 6 equine), as described by Parreira et al. (2012). Briefly, DNA plugs for PFGE were prepared from overnight cultures of *C. perfringens* grown in TGY (3% Tryptic Soy Broth [Difco] containing 2% D-glucose [Difco], 1% yeast extract [Difco], and 0.1% L-cysteine [Sigma-Aldrich]) and the bacterial pellets incorporated into a final agarose concentration of 1% in PFGE certified agarose (Bio-Rad Laboratories, Hercules, Calif.). Plugs were incubated overnight with gentle shaking at 37° C. in lysis buffer (0.5M EDTA pH 8.0, 2.5% of 20% sarkosyl [Sigma-Aldrich], 0.25% lysozyme [Sigma-Aldrich]) and subsequently incubated in 2% proteinase K (Roche Applied Science) buffer for 2 days at 55° C. One-third of a plug per isolate was equilibrated in 200 μl restriction buffer at room temperature for 20 min and then digested with 10 U of NotI (New England Biolabs, Pickering, ON) at 37° C. overnight. Electrophoresis was performed in a 1% PFGE-certified gel and separated with the CHEF-III PFGE system (Bio-Rad) in 0.56 Tris-borate-EDTA buffer at 14° C. at 6 V for 19 h with a ramped pulse time of 1 to 12 sec. Gels were stained in ethidium bromide and visualized by UV light. Mid-Range II PFG markers (New England Biolabs) were used as molecular DNA ladder.

Preparation of DIG Probes and PFGE Southern Blotting:

DNA probes for all PFGE Southern blot steps were labelled by PCR amplification in the presence of digoxigenin-11-dUTP (DIG; Roche Applied Science) according to the manufacturer's recommendation. DNA probes were amplified from *C. perfringens* strain CP1. DNA probes for netE and cpe genes were prepared with NetE and Cpe probe primers (Table 1). DNA from PFGE gels was transferred to nylon membranes (Roche Applied Science). DNA hybridizations and detection were performed by using the digoxigenin (DIG) labelling and CSPD (disodium 3-(4-methoxyspiro {1,2-dioxetane-3,2'-(5'-chloro)tricyclo[3.3.1.13,7] decan}-4-yl)phenyl phosphate) substrate according to the manufacturer's recommendation (Roche Applied Science). For Southern blot hybridizations, nylon membranes were pre-hybridized for at least 2 h at 42° C. in hybridization solution without labelled probe and then hybridized separately at 42° C. with specific DNA probes for 16 h. The membranes were washed at 68° C. under high-stringency conditions. For each different DIG labelled probe, the membrane was first stripped with 0.2 N NaOH and 0.1% sodium dodecyl sulfate, incubated with pre-hybridization solution, and then re-probed.

Figure 2A:
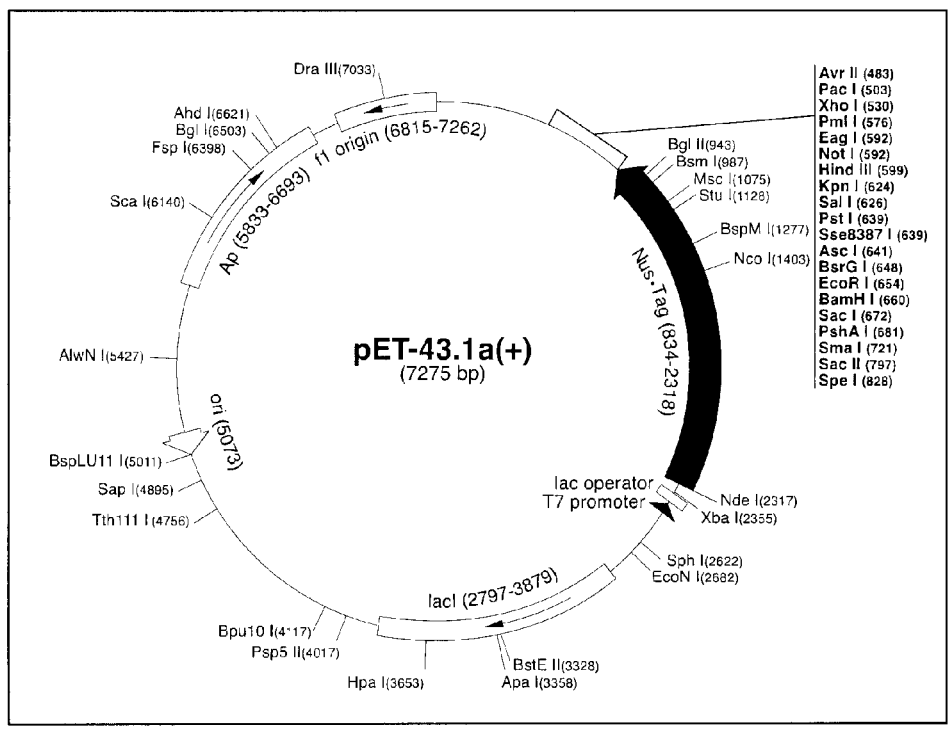
FIGS. 2A and B show the modification of pET43.1a. Enzymatic digestion was performed in pET41.1a into the restriction sites SpeI and XmaI to remove the His tag of NusA. The sequences of the pET-43.1a(+), pET-43.1b(+) and pET-43.1c(+) are also shown in SEQ ID NOs: 20-22, respectively.
Figure 2B:
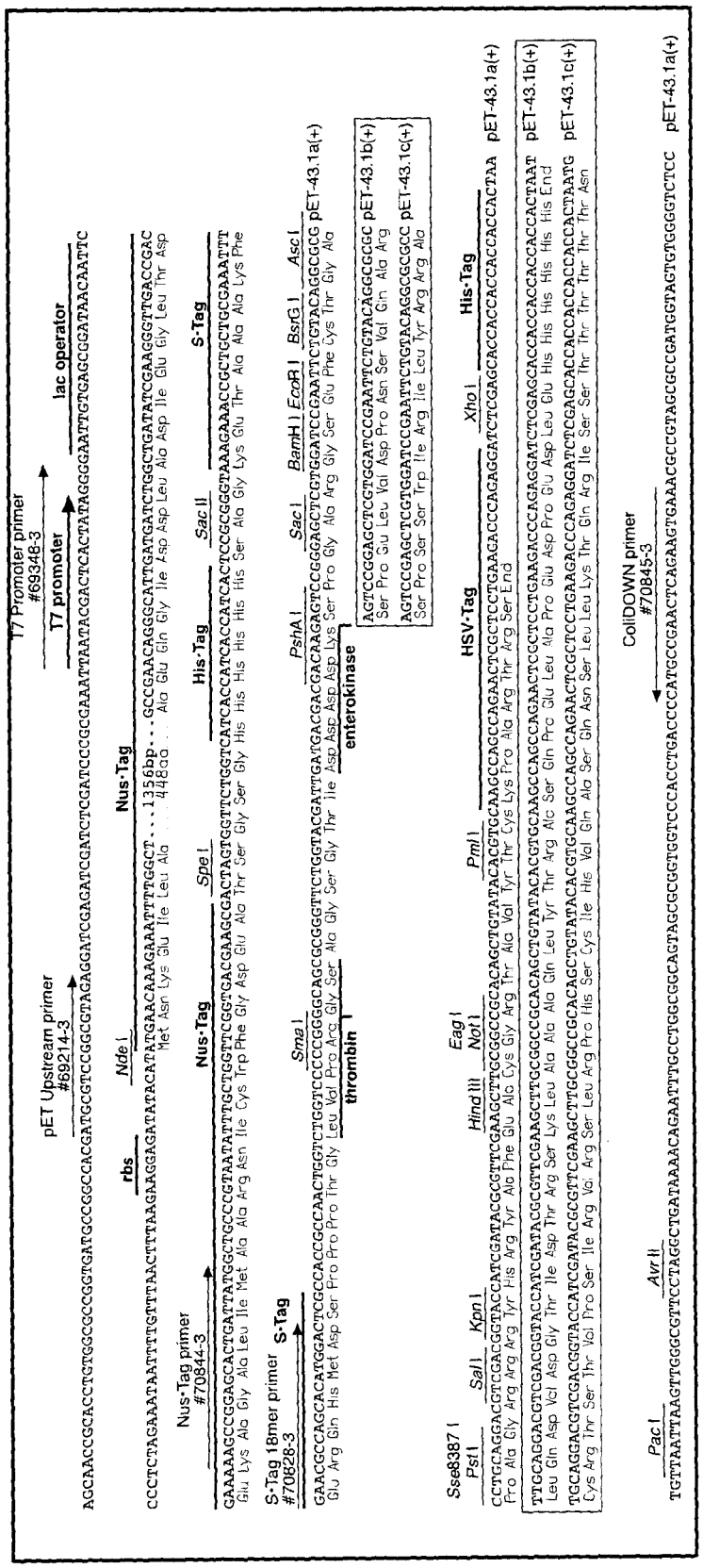

Cytotoxicity Screening of Supernatants of *Clostridium perfringens* Isolates, and Toxicity in Relation to Growth Broth culture supernatants of *C. perfringens* isolates were evaluated for cytotoxicity in vitro. *Clostridium perfringens* isolates were streaked onto blood agar plates and grown anaerobically overnight at 37° C. A single colony of each isolate was then inoculated into 5 ml TPG and grown anaerobically at 37° C. for ~16 h. Following incubation, 50 μl was inoculated into 5 ml (1:100 v/v) of fresh TPG and grown for ~3 h at 37° C. to an optical density at 600 nm ($OD_{600}$) of 0.6-0.8 (Novaspec Plus spectrophotometer, Biochrom, Cambridge, UK). The broth cultures were then centrifuged at 18,000×g for 15 min before filtering through a 0.22 μm syringe filter to obtain a sterile filtrate.

Toxicity was tested against an equine ovarian cell line (Dr. E. Nagy, Department of Pathobiology, University of Guelph). One hundred μl of EMEM complete medium (EMEM 450 ml, 10% fetal calf serum [VWR International, Radnor, Pa.]) was added to a 96-well cell culture cluster flat bottom with lid plates (Corning Incorporated, Corning, N.Y.) and seeded with ~$2\times10^5$ equine ovarian cells/well according to the formula:

$$\text{Volume (ml) to add per well}=(2\times10^5\text{ cells/well})/(\text{Number of cells/ml}).$$

The plate was then incubated in a 5% $CO_2$ incubator for 24-36 h until cells were almost 100% confluent. The EMEM medium was then removed from the wells and 100 μl of complete EMEM, but with only 5% fetal calf serum, was added to each well. Subsequently, 100 μl of sterile bacterial culture supernatant was added to the wells, in a 2-fold dilution series up to 1:1024 (v/v) in duplicate for each strain tested. Cytotoxicity effects were evaluated by checking cells microscopically after eight hours. The scoring for the toxicity screening is presented in FIGS. 1(A-E); the cytotoxicity end-point was 2+.

Host Cell Cytotoxicity Specificity:

The following cell lines were assessed for susceptibility to the supernatant of netE-positive strains: Madin Darby Bovine Kidney cell line, MDBK (ATCC, CCL-22); Porcine Kidney cell line, PK15 (ATCC, CCL-33); the Rat Fischer Fibroblast cell line, 208F (Life Technologies, ON); the Mouse Embryo Fibroblast cell line, NIH 3T3 (ATCC, CRL-1658); the African green monkey kidney cell line, Vero (ATCC, CCL-81); the human colon epithelial cell line, CaCo-2 (ATCC, HTB-37); these were grown in EMEM complete media. The A72, a cell line derived from canine fibroblasts, was maintained in Dulbecco's Modified Eagle Medium (DMEM) supplemented with 10% fetal calf serum [VWR International], 2 mM L-glutamine [Sigma-Aldrich]. The primary chicken hepatocellular carcinoma epithelial cell line, LMH (ATCC, CRL-2117) was grown in Waymouth's complete media (90% Waymouth's MB 752/1 [Invitrogen, ON], 10% fetal calf serum [VWR International]). Tissue culture vessels used to propagate this line were pre-coated with 0.2% gelatin. All cell lines were incubated in 5% $CO_2$ at 37° C. until almost 100% confluence in 96-well plates. To test cytotoxicity, culture supernatant of NetE-producing strains was added to the medium and diluted in two-fold steps across the plate, to a dilution of 1:1024, and incubated for 8 h at 37° C. as described. The cytopathic effect was assessed as described; the cytotoxicity of the culture supernatant of a netE-positive strain on the equine ovarian cell line was used as a control for comparison.

NetE Toxin Production in Relation to Bacterial Growth:

The production of cytotoxicity by an equine netE-positive strain (JP728) was compared against growth of the strain. Overnight culture of NetE producing strain was diluted to an optical density at 600 nm ($OD_{500}$) of 0.8. Then 2.5 ml of culture was inoculated into 50 ml of fresh TPG broth and grown anaerobically at 37° C. for 48 h. Samples were withdrawn at 2 h intervals for up to 16 h and again at 24 and 48 h to determine the $OD_{600}$ values and toxicity screening on the equine ovarian cell line. Supernatants were also analyzed for NetE production using SDS-PAGE and Western blot, as described below under Western blot analysis.

Purification of NetE Using Recombinant Protein Techniques

Purification of Recombinant NetE Using pET-28a (+) Vector:

DNA of strain JP728 was isolated as described above and used as a template in PCR reactions. PCR reactions were performed with a Platinum PCR SuperMix high-fidelity kit (Invitrogen). Primers used for recombinant construction of the recombinant protein are described in the Table 1. PCR products were purified by using a Gel Extraction Kit (Qiagen) and cloned into the pET28a vector (Novagen, Gibbstown, N.J.), then transformed into *E. coli* DH5a. The nucleotide sequences of the cloned PCR products were verified by sequencing. The plasmid carrying the netE gene with N-terminal and C-terminal 6 His-Tags were introduced into *E. coli* BL21 (DE3) pLysS competent cells (Promega, Wis.), following the manufacturer's instructions. Cells were grown in LB medium with 50 μg/ml kanamycin and 34 μg/ml chloramphenicol at 37° C. until the absorbance at 600 nm reached 0.5, and then induced by adding 1 mM isopropyl-b-D-thiogalactopyranoside (IPTG) at 37° C. for four hours. Purification of His-tagged NetE protein from *Escherichia coli* BL21 was performed under native and denaturing conditions according to the manufacturer's instructions with minor modifications (Qiagen). Purification of rNetE was attempted under native conditions, but the protein was found to be insoluble, so that purification was performed under denaturing conditions.

For purification of rNetE under denaturing conditions, the cell pellet (1.0 g wet weight) saved from the above was resuspended in 5 ml of lysis buffer (100 mM $NaH_2PO_4$, 10 mM Tris-Cl, 8M Urea, pH 8.0). The mixture was stirred for 60 min at room temperature. The lysate was centrifuged at 10,000×g for 30 min at room temperature to harvest the cellular debris. One ml of the 50% affinity chromatography on nickel-nitrilotriacetic acid agarose (Ni-NTA) was added to cleared lysate and mixed gently on a shaker for 60 min. The lysate-slurry mixture was loaded into the column (Qiagen). The column was washed twice with 4 ml of 100 mM $NaH_2PO_4$, 10 mM Tris-Cl, 8 M Urea, pH 6.3, followed by 4 times with 1 ml 100 mM 100 mM $NaH_2PO_4$, 10 mM Tris-Cl, 8 M Urea, pH 5.9, and rNetE eluted with 4 times 0.5 ml 100 mM $NaH_2PO_4$, 10 mM Tris-Cl, 8 M Urea, pH 4.5. Subsequently, dialysis approach was performed to remove the denaturing agent (urea) and to attempt to re-nature rNetE to its native conformation. Dialysis was done by gradually removing urea from 6M to 1M. Dialysis stopped in 1M urea, since rNetE was precipitated in lower concentration of urea. The final products were characterized by SDS-PAGE analysis.

Purification of Recombinant NetE Using the Fusion Partner rNetE-NusA for Expression of Soluble Protein:

To improve rNetE protein expression and solubility, a heterologous soluble protein NusA, which acts as a molecular chaperone to aid in protein folding, was fused with rNetE protein (Table 3). The NusA (45 kDa), as solubility enhancing tag in *E. coli*, was fused to NetE N-terminus into pET43.1a vector. A modified pET43.1a (mpET43.1a) was constructed in order to eliminate the His-tag of NusA protein and facilitate purification of rNetE protein. The mpET43.1a was obtained by digesting the vector with restriction enzymes SpeI to XmaI thus removing a region containing His-tag and then re-ligating the vector again (FIG. 2). The PCR amplified netE gene was cloned into the EcoRI and HindIII sites of modified vector pET43.1a (Novagen) to express His-tagged rNetE::NusA fusion protein in *E. coli* BL21 (DE3) pLysS. Cells were grown in LB medium with 100 μg/ml ampicillin and 34 μg/ml chloramphenicol at 37° C. until the absorbance at 600 nm ($OD_{600}$) reached 0.5, and then induced by adding 1 mM IPTG at 37° C. for overnight. The histidine-tagged protein was purified under native conditions using Ni-NTA agarose following the manufacturer's instructions (Novagen). Purification of rNetE::NusA was done by nickel chelation chromatography as described by the manufacturer. Cleavage of the NusA from the recombinant protein to obtain rNetE was done using the enterokinase cleavage capture kit (Novagen) (Table 3) which resulted in a protein with a molecular mass of 35 kDa. To remove the NusA protein from the mixture, a second round of purification by Ni-NTA was performed. The resulting protein expression and solubility levels were evaluated by SDS gel electrophoresis before and after protein purification and after NusA removal.

Production of Polyclonal and Monoclonal Antibodies to rNetE

Rabbit Polyclonal Antibody:

His-tagged denatured recombinant NetE was used for polyclonal antibody production in rabbits (Cedarlane Laboratories Limited, Burlington, ON). The denatured protein in 1M urea, 500 mM NaCl, 50 mM Tris-HCl pH7.5 and 5% glycerol was used. A 1:1 ratio of Incomplete Freunds Adjuvant (IFA) and sterile antigen (rNetE) was mixed together using 0.2-0.5 mg of antigen for a total of 1-2 mL per rabbit depending on size. Rabbits were immunized subcutaneously on day 0, 28, 47, and 66, and bled at these times. A terminal bleed was on day 78 after initial immunization.

Figure 3:
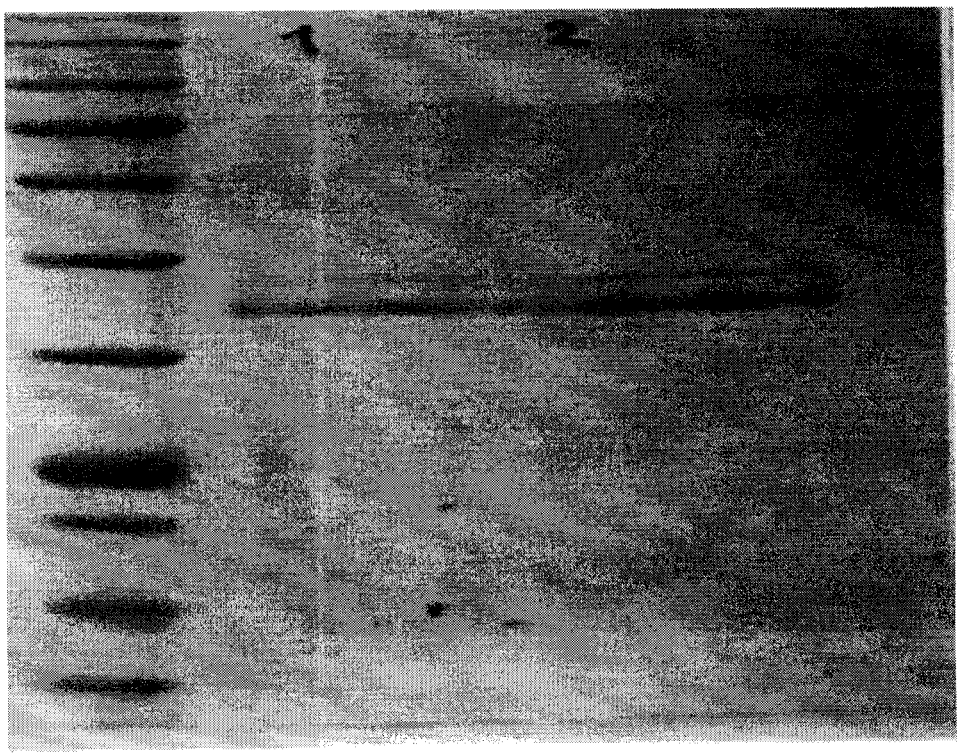
FIG. 3 shows electro-eluted denatured rNetE from polyacrylamide gel that was sent to ImmunoPrecise Antibodies Ltd. (Victoria, BC, Canada) for raising monoclonal antibody in mice.

Mouse Monoclonal Antibody Production:

rNetE electro-eluted from SDS-PAGE gel was sent to ImmunoPrecise Antibodies Ltd. (Victoria, BC) for monoclonal antibody production in mice. For preparation of electro-eluted protein, rNetE protein was electrophoresed on a 12% polyacrylamide gel and the zone with rNetE then cut from the gel. The gel strip containing rNetE was cut into small pieces and placed in electro-elution tube containing electrophoretic buffer (25 mM Tris base, 192 mM Glycine and 0.1% SDS). A dialysis lid at the bottom of the tube held the gel slices within the tube. The electro-elution tube subsequently was inserted into an electro-elution apparatus containing the same electrophoretic buffer. rNetE was electro-transferred from polyacrylamide gel into the dialysis sack, and the SDS was later removed from the sample by dialysis. One hundred μg of electro-eluted antigen (FIG. 3) emulsified in Incomplete Freunds Adjuvant (IFA) was used to immunize four female BALB/c mice (25 μg/mouse) intraperitoneally. Booster injections of immunogen materials were done at 21 days intervals. Mice sera were collected 10 days following the second boost and were checked for specific antibody titer by ELISA. The top two responding mice were immunized with a final antigen intravenous boost and used as spleen donors cell fusion and hybridoma cell line generation. Spleen cells were purified and fused with murine SP2/0 myeloma cells in the presence of polyethylene glycol. Fused cells were cultured using IPA's propriety 1-step cloning method. Ten days after fusion step, up to 948 of the resulting hybridoma clones were transferred to 96-well tissue culture plates and grown in HT containing medium until mid log growth was reached. Then, hybridoma tissue culture supernatants were transferred to antigen coated ELISA plates and indirect ELISA was employed with secondary antibody for both IgG and IgM monoclonal antibodies. Positive cultures were retested on immunizing antigen to confirm secretion and on an irrelevant antigen (human transferrin) to eliminate non-specific monoclonal antibodies and rule out false positives. Subsequently, the hybridoma cell lines were maintained in culture for 32 days post transfer to 96-well culture plates and sub-cloned to ensure stability and secretion.

Horse Immunization:

The rNetE-NusA fusion protein was used for polyclonal antibody production in three adult horses. A 1:4 ratio of aluminium hydroxide gel and sterile antigen was mixed together using 2.0 mg of antigen in 2 ml 50 mM $NaH_2PO_4$-300 mM NaCl-150 mM imidazole, for a total of 2.5 ml per horse. For the primary immunization cleaved rNetE-NusA protein mixture and for the two subsequent immunizations the fusion rNetE-NusA protein was used. Horses were immunized intramuscularly at day 0, 14, and 28, and bled at these times as well as on day 35 and 42 after initial immunization. Horses were examined for four days after each immunization and body reactions to injected antigen were recorded.

Development of Tests (Neutralization, ELISA, Western Immunoblot) for rNetE Antibodies Cytotoxin Neutralization by Antibody to rNetE:

The ability of horse or rabbit polyclonal rNetE antibodies and of mouse monoclonal rNetE antibody to protect the equine ovarian cell line against supernatant of a netE-positive strain was also assessed. The cytotoxicity neutralization test was performed with the equine ovarian cell line. An overnight culture supernatant of a netE-positive strain (JP728) was prepared as described under cytotoxicity screening. The supernatant was diluted in EMEM medium; the dilution of supernatant used for determination of neutralization titers was 128. Subsequently, serial 2-fold dilutions of antibodies within sera up to 1:131,072 were made in a new 96-well plate (100 μl/well). Diluted antibodies were transferred into the diluted toxin plate and manually homogenized for 30 seconds and incubated for 2 h at 37° C. After incubation, 100 μl of the toxin-antibody dilution series was added into confluent equine ovarian cell line plate and the plate incubated in a humidified environment of 5% $CO_2$ at 37° C. for 8 h. The neutralizing antibody titer was defined as that showing an inhibition of 2+ or greater (Roth et al., 1999).

Enzyme-Linked Immunosorbent Assay (ELISA):

For ELISA, 96-well plates (MaxiSorp, Nunc, Roskilde, Denmark) were coated with 0.1-0.5 μg/well of electro-eluted rNetE in carbonate-bicarbonate buffer pH 9.6 for 1 h at 37° C. followed by overnight incubation at 4° C. After washing the plate twice with wash buffer (PBS, 0.05% Tween 20) and once using phosphate-buffered saline, pH 7.4 (PBS), the coated plate was blocked using blocking buffer (PBS, 0.05% Tween 20, 0.5% fish skin gelatin [Norland HiPure Liquid Gelatin, Norland Products Inc, Cranbury, N.J.]) for 2 h at 37° C. After washing 3 times with wash buffer, 100 µl/well of horse polyclonal antibodies (two-fold serial dilutions up to 1:409600) were added to the plate in duplicate. Washing buffer with no polyclonal antibodies was used as a negative control. After incubation at room temperature for 2 h, followed by 3 times washings with washing buffer, 100 µl/well of enzyme-labeled detecting goat anti horse antibody (diluted 1:5000 in wash buffer) was applied, and the plate was incubated for another 1 h at room temperature. The plate was then washed 3 times with wash buffer and 100 µl/well of the chromogenic substrate 2,2'-azino-di-[3-ethylbenzthiazoline sulfonate]diammonium salt (ABTS) (Roche Applied Science) was added. After 30 min to 1 h further incubation at room temperature, the reaction was stopped using 0.5% SDS (50 µl/well) and the OD measured at 405 nm (OD405) in an ELISA reader (BioTek Instruments Inc., Power Wave XS, Winooski, Vt.) (Kircanski et al., 2012b).

Western Blot Analysis:

Western immunoblotting was used to assess the specificity of rabbit polyclonal and mouse monoclonal antibodies against rNetE. For this purpose, two type B *C. perfringens* (NCTC3110, NCTC7368), two type C *C. perfringens* (ATCC3628, NCTC3181), and two netB-positive (CP1, CP4), strains were grown anaerobically in TPG broth overnight at 37° C. Culture supernatant fluids were obtained by centrifugation at 18,000×g for 15 min at 4° C. Supernatants containing proteins were mixed with a 1:1 ratio of Laemmli Sample Buffer (Bio-Rad) and separated by SDS-PAGE in 12% acrylamide gel at room temperature. Proteins were compared to BLUeye Prestained Protein Ladder (FroggaBio, ON).

Subsequently, proteins were transferred onto a nitrocellulose 0.45 µm membrane (BioTrace NT, Gelman Laboratory, Laurent, QC) for 60 min at constant power supply of 95 V. Then, blotting membrane was blocked overnight in blocking buffer (PBS, 0.05% Tween 20, 0.5% fish skin gelatin). The blocking period was followed by incubation with primary antibody. For all the samples 2 Western blots were performed since 2 types of primary antibodies were used, polyclonal rabbit antibody and monoclonal, at 1:50000 and 1:1000 dilutions (v/v) respectively. Membranes were incubated for 90 min at room temperature. After 3 times washing, the membranes were incubated with alkaline phosphatase-conjugated goat anti-rabbit IgG and alkaline phosphatase-conjugated goat anti-mouse IgG (Jackson ImmunoResearch Laboratories Inc., West Grove, Pa.) at 1:5000 dilution. Specific protein bands were visualized using the Alkaline Phosphatase Conjugate Substrate Kit (Bio-Rad) (Kircanski et al., 2012a).

Results

Identification of Toxicity in a Type A *Clostridium perfringens* Isolated from a Foal with Fatal Necrotizing Enteritis: The Discovery of NetE A type A *C. perfringens* (strain JP728) was isolated from a fatal case of necrotizing small intestinal enteritis. The supernatant of this bacterium, grown in TPG to an OD$_{600}$ 0.6-0.8, was found to be highly toxic for an equine ovarian cell line in comparison to a beta toxin (CPB) or enterotoxin (CPE) producing strain (Table 2). Table 2 shows the greater toxicity of this supernatant than of strains producing other known toxins.

Identification of a Novel Necrotizing Toxin Gene, netE, in JP728 Plasmid Sequence Plasmid DNA was isolated from strain JP728 and sequenced as described on the Roche 454 GS Junior system (Roche Applied Science). Sequence annotation of pNetE-JP728 showed the presence of 158 open read frames (orfs). Sequence analysis identified a toxin with 79% amino acid homology to the NetB toxin and 39% homology to the beta toxin of *Staphylococcus aureus*, belonging to the Leukocidin superfamily, a family of pore-forming and beta-channel forming cytolytic proteins (FIG. 4; Table 3). This putative toxin gene was designated NetE and has also been called Toxin E. Subsequent PCR amplification of the netE gene from 3 canine hemorrhagic enteritis isolates and two other foal necrotizing small bowel enteritis isolates showed the netE genes to be identical in nucleotide sequence.

Figure 5:
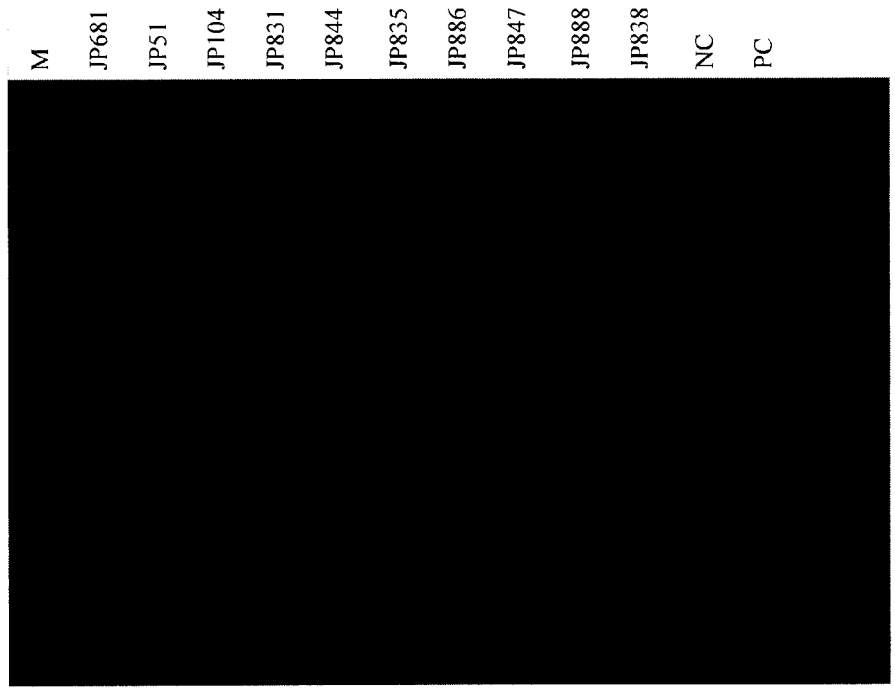
FIG. 5 shows PCR amplification of the netE gene. M: 100 bp DNA ladder marker (New England Biolabs), PCR amplification from each specified C. perfringens strains, NC: negative control and PC: positive control.

Association of netE with Specific Disease of Animals, with Cytotoxicity, and with Other Toxin Genes A PCR was developed for netE, as illustrated in FIG. 5.

Using this PCR, the netE gene was identified in 9 of 11 isolates (82%) from different foals with severe necrotizing enteritis compared to 6% of 79 isolates from individual (usually adult) horses with undifferentiated diarrheal disease ($P<0.0001$, Fisher's exact test).

The netE gene was identified in 7 of 9 isolates (78%) from canine hemorrhagic gastroenteritis compared to 13% of 84 undifferentiated canine diarrheal isolates ($P<0.0001$, Fisher's exact test). The netE gene was not yet identified in any of bovine (58), human (39) or porcine (56) isolates from animals or people with undifferentiated diarrhea.

The supernatant of seven canine and seven equine netE-positive isolates produced under the conditions described was as toxic as that of JP728 to the ovarian cell line, in comparison to 50 netE-negative strains which showed no toxicity.

PCR analysis of netE-positive isolates from cases of foal necrotizing enteritis or canine hemorrhagic enteritis (n=15) showed that the netE gene was always (100%) found in association with the cpe enterotoxin gene and in 67% of isolates with the cpb2 gene, compared, respectively, to 26% and 35% of 151 canine and equine netE-negative strains ($P<0.001$).

The Plasmid Localization of netE and the Cpe Genes

Figure 6:
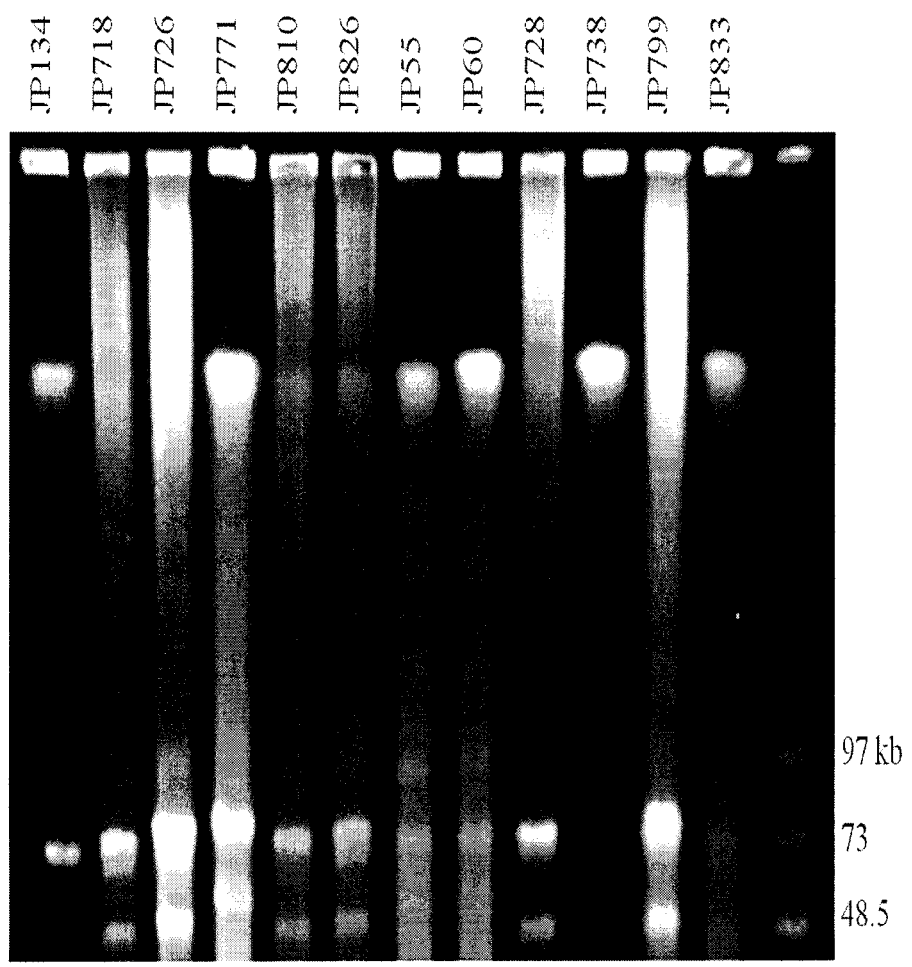
FIG. 6 shows pulse field gel electrophoresis (PFGE) of plasmids from equine and canine C. perfringens strains. Agarose plugs containing DNA from each specified isolate were digested with NotI and subjected to PFGE and staining with ethidium bromide. Line numbers indicate isolate numbers M: Mid-Range II PFG molecular DNA ladder (Kb).
Figure 7:
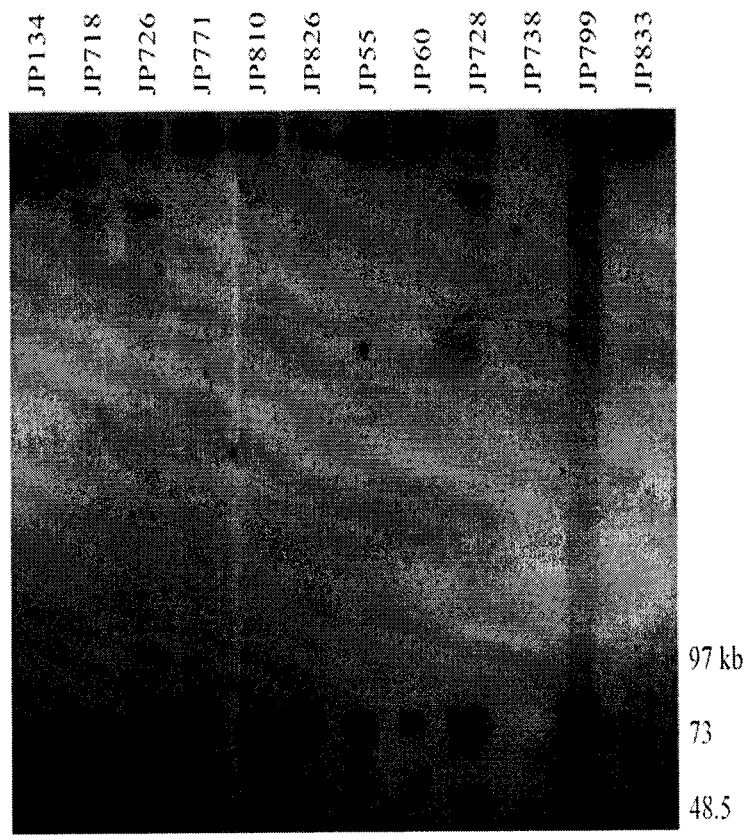
FIG. 7 shows PFGE Southern blot of plasmids from equine and canine C. perfringens. Southern blotting of PFGE was performed with DIG-labelled probes for netE and cpe. Results from both netE and cpe probes are shown overlaid. In all lanes with two bands, the upper band represents netE and the lower band cpe. M: Mid-Range II PFG molecular DNA ladder (Kb).

To determine the presence of large plasmids in equine and canine *C. perfringens* strains, the DNA of 12 strains were subjected to pulsed-field gel electrophoresis (PFGE). The PFGE profiles of the *C. perfringens* strains digested with NotI revealed the presence of 2 large plasmids ranging in size from 45 kb-75 kb in all strains (FIG. 6). Most isolates carried at least 2 large plasmids. Southern blotting of PFGE showed the presence of netE and cpe on different plasmids. Hybridization to ~40 kb to 75 kb bands confirmed the plasmid identity of these PFGE bands and showed that the netE gene was always located in the larger plasmids (FIG. 7). The cpe probe hybridized to different and smaller plasmids than the netE probe (FIG. 7).

Toxicity in Relation to Growth, and Cell Line Specificity

Figure 8:
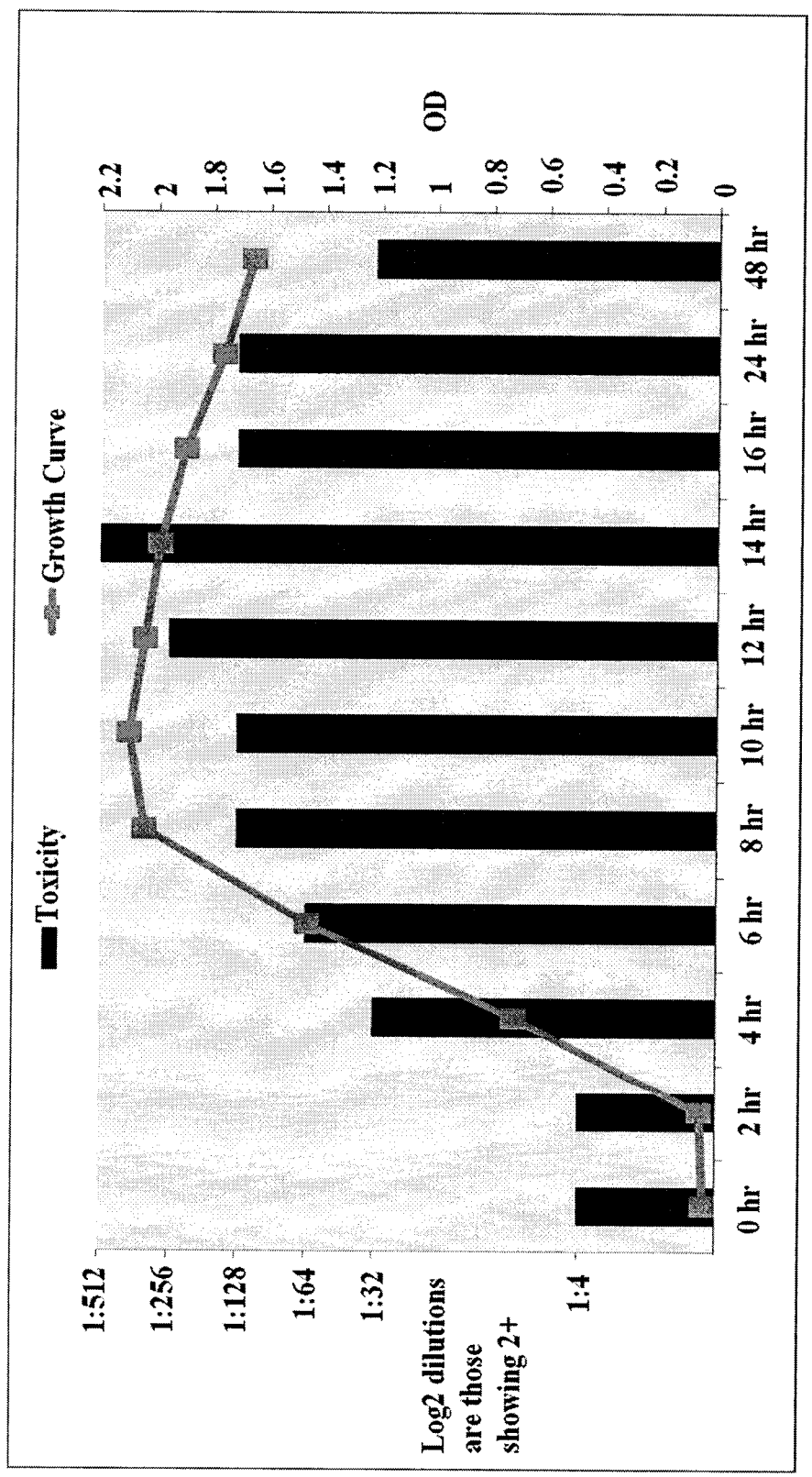
FIG. 8 shows comparison of toxicity and growth curve of netE-positive strain growth. The horizontal axis shows the time of withdrawing samples at 2 h intervals up to 16 h and two more samples at 24 and 48 h. The right vertical axis shows the optical density at 600 nm. The left vertical axis shows $\log_2$ toxicity dilutions. End-point toxicity was 2+. The highest NetE expression and toxicity was at the beginning of stationary phase.
Figure 9:
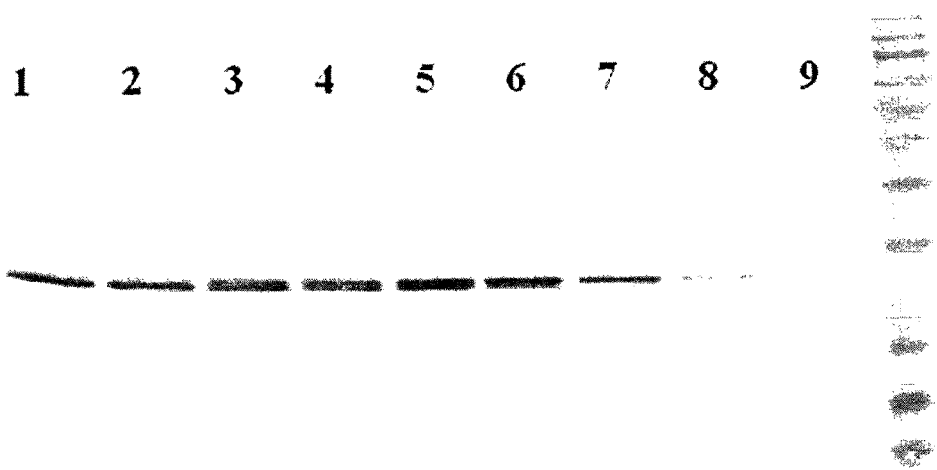
FIG. 9 shows confirmation of NetE expression level by Western blot. Lane (1): 4 h culture (OD: 0.72); Lane (2): 6 h culture (OD: 1.496); Lane (3): 8 h culture (OD: 2.041); Lane (4): 10 h culture (OD: 2.099); Lane (5): 12 h culture (OD: 2.04); Lane (6): 14 h culture (OD: 1.99); Lane (7): 16 h culture (OD: 1.90); Lane (8): 24 h culture (OD: 1.766); Lane (9): 48 h culture (OD: 1.666). Western blot confirms that the highest NetE expression was at the beginning of stationary phase.

Growth and Toxicity:

FIG. 8 shows the relationship between toxicity of the supernatant of strain JP728 in relation to growth determined by optical density. Analysis of supernatant fractions using the mouse monoclonal confirmed that maximal amounts of NetE were produced in early stationary phase of growth (FIG. 9).

Cytotoxicity of Canine and Equine Source netE-Positive Isolates for Cell Lines from Different Animal Species:

Cytotoxicity of canine and equine netE-positive isolates were compared with cpb-positive isolate for cells lines from different species (Table 4). Both strains were highly toxic to the equine ovarian cell lines, but other cell lines were not as susceptible. However, the two canine cell lines were the second most susceptible of the cells tested.

Purification of Recombinant NetE

Figure 10:
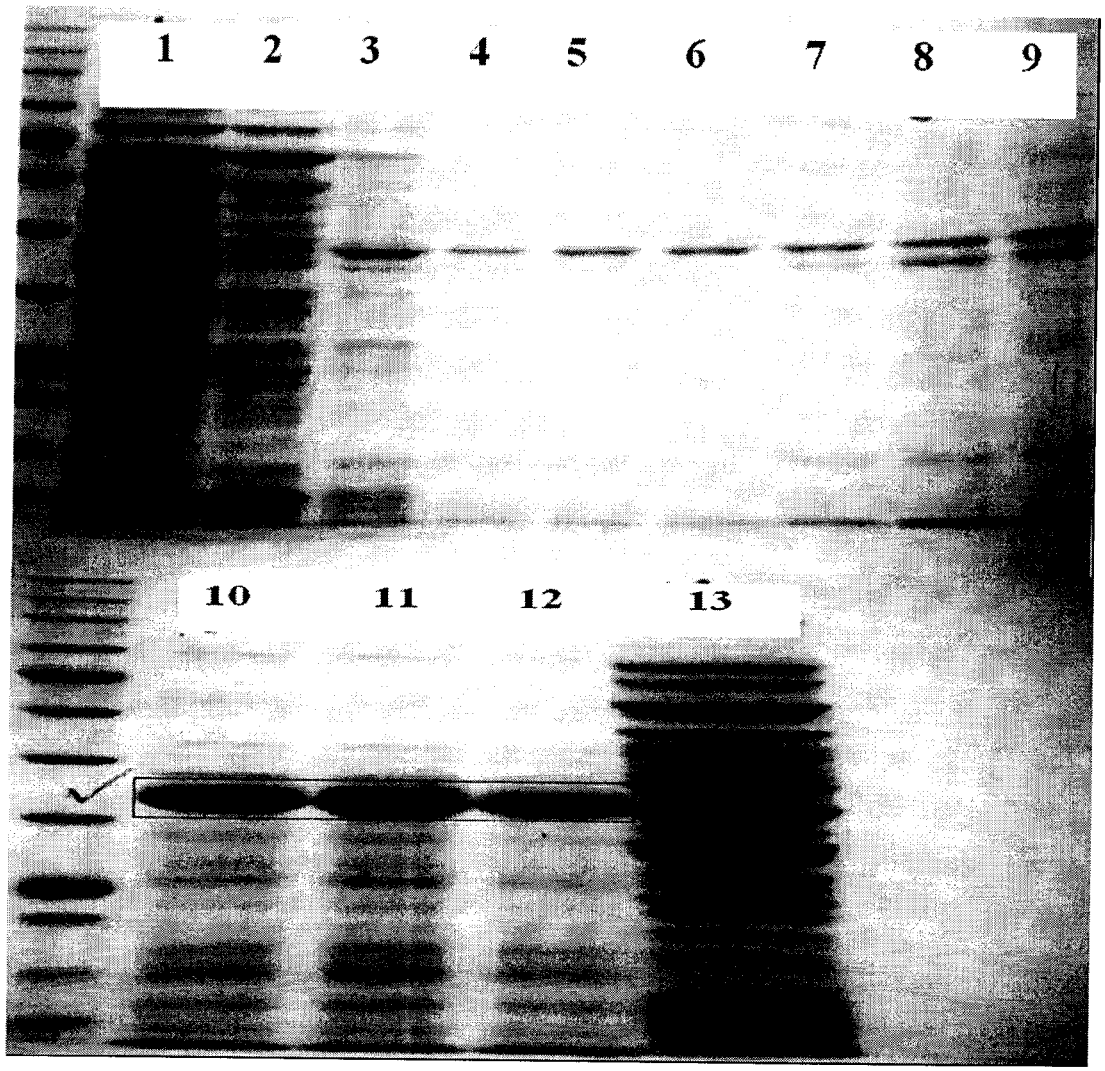
FIG. 10 shows purification of rNetE (pET-28a-c vector) under denaturing conditions. Lane (1): Lysate sample; Lane (2): Flow-Through; Lane (3): Wash fraction 1 (pH: 6.3); Lane (4): Wash fraction 2 (pH: 6.3); Lane (5): Wash fraction 1 (pH: 5.9); Lane (6): Wash fraction 2 (pH: 5.9); Lane (7): Wash fraction 3 (pH: 5.9); Lane (8): Wash fraction 4 (pH: 5.9); Lane (9): Elute fraction 1 (pH: 4.5); Lane (10): Elute fraction 2 (pH: 4.5); Lane (11): Elute fraction 3 (pH: 4.5); Lane (12): Elute fraction 4 (pH: 4.5); Lane (13): Pellet sample. Purification under denaturing conditions determined that rNetE was soluble in 8M urea.

SDS-PAGE analysis of purification of rNetE using the his-tagged pET-28a vector under native conditions determined that rNetE was insoluble in this vector. Therefore, denaturing conditions were applied for purification and rNetE was found to be soluble in 8 M urea (FIG. 10). Subsequently, dialysis approach was performed to attempt to re-nature to its native conformation by removing urea; the protein precipitated in urea amounts less than 1 M. Denatured protein in 1 M urea was used to immunize rabbits and was electro-eluted from the polyacrylamide gels to produce protein for mouse monoclonal antibody production and to coat plates for ELISA.

Figure 11:
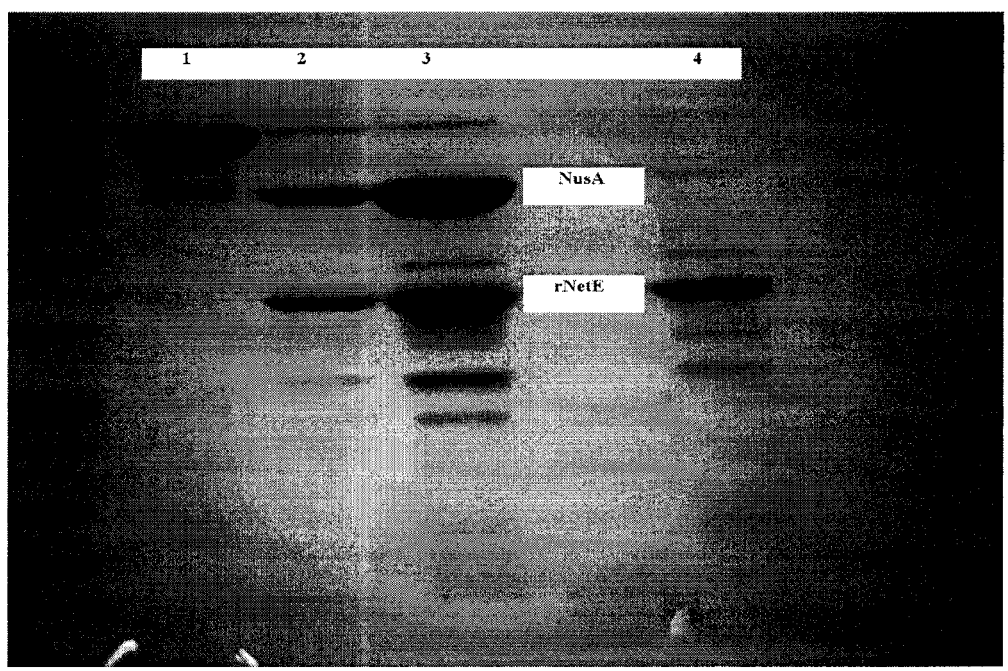
FIG. 11 shows production and purification of soluble rNetE through modified pET 43.1a vector. Lane (1): Fusion Nus-NetE protein. Lane (2&3): Cleaved Nus-NetE protein. Lane (4): Purified rNetE protein.

The NusA fusion protein improved protein expression and solubility of rNetE protein. Cleaved rNetE from NusA fusions were soluble since NusA acts as an effective solubility enhancer. The results of overexpression of fusion proteins in *E. coli* at 37° C. are shown in FIG. 11. The SDS-PAGE and Western blot results show that the fusion proteins rNetE-NusA were expressed at a high level.

Production of Polyclonal and Monoclonal Antibodies to rNetE

Figure 12:
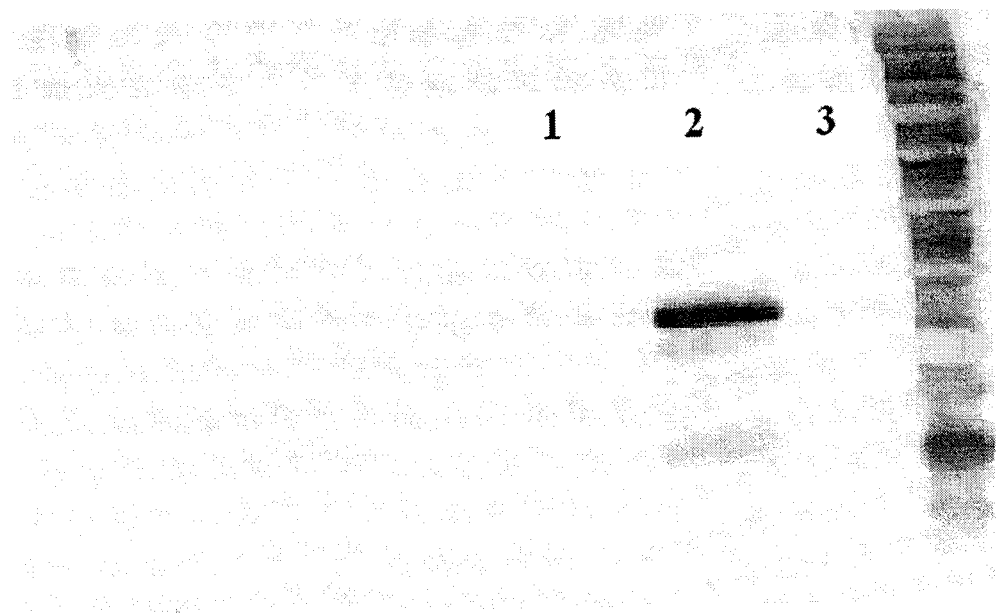
FIG. 12 shows rabbit polyclonal antibody against NetE. Lane (1): 100× concentrated supernatant of netE-negative strain (JP58). Lane (2): 100× concentrated supernatant of netE-positive strain (JP728). Lane (3): Non-concentrated supernatant of netE-positive strain showing a very faint NetE band (JP728).
Figure 13:
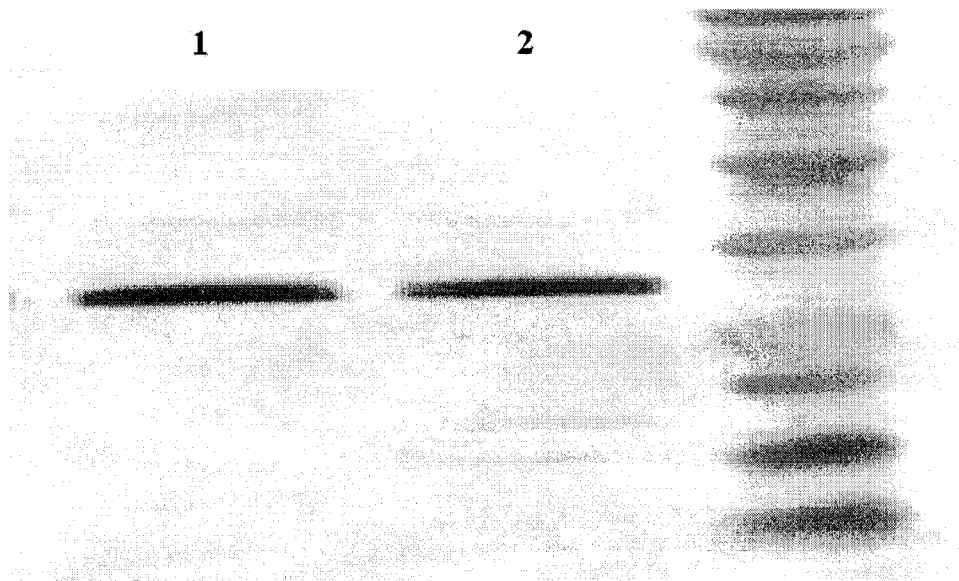
FIG. 13 shows mouse monoclonal antibody against NetE. Lane (1): Culture supernatant of equine netE-positive strain (JP728). Lane (2): Culture supernatant of canine netE-positive strain (JP726).

Rabbit Polyclonal and Mouse Monoclonal Antibodies:

Polyclonal antibodies to rNetE were successfully produced in rabbits (FIG. 12) and a monoclonal antibody in mice (FIG. 13). Pre-treatment of rabbit polyclonal antibodies with culture supernatant of netE-positive strain neutralized the toxicity of bacterial supernatant for the equine ovarian cell line whereas pre-incubation with pre-immune serum did not. The neutralization titer was 1:512. Cytotoxin neutralizing antibody was present in 5 different mouse hybridoma cells at dilutions of 1:2.

Figure 14:
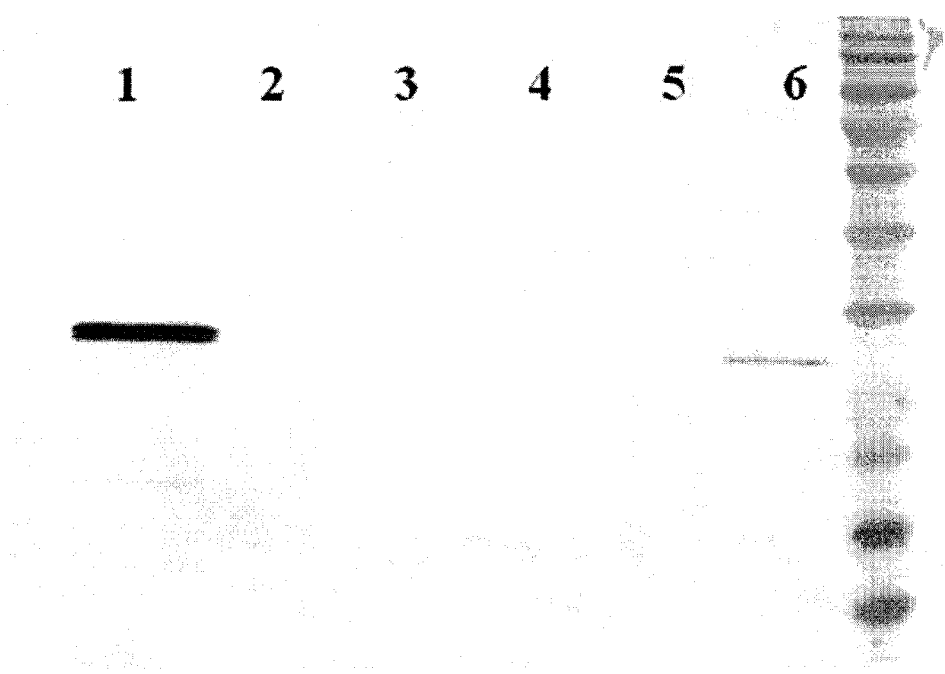
FIG. 14 shows polyclonal antibody specificity. Lane (1): JP728 (NetE+); Lane (2): NCTC3110 (Type B); Lane (3): NCTC7368 (Type B); Lane (4): ATCC3628 (Type C); Lane (5): NCTC3181 (Type C); Lane (6): CP4 (NetB+). Rabbit polyclonal antibody is specific for NetE. There is a minor cross-reaction only with NetB.
Figure 15:
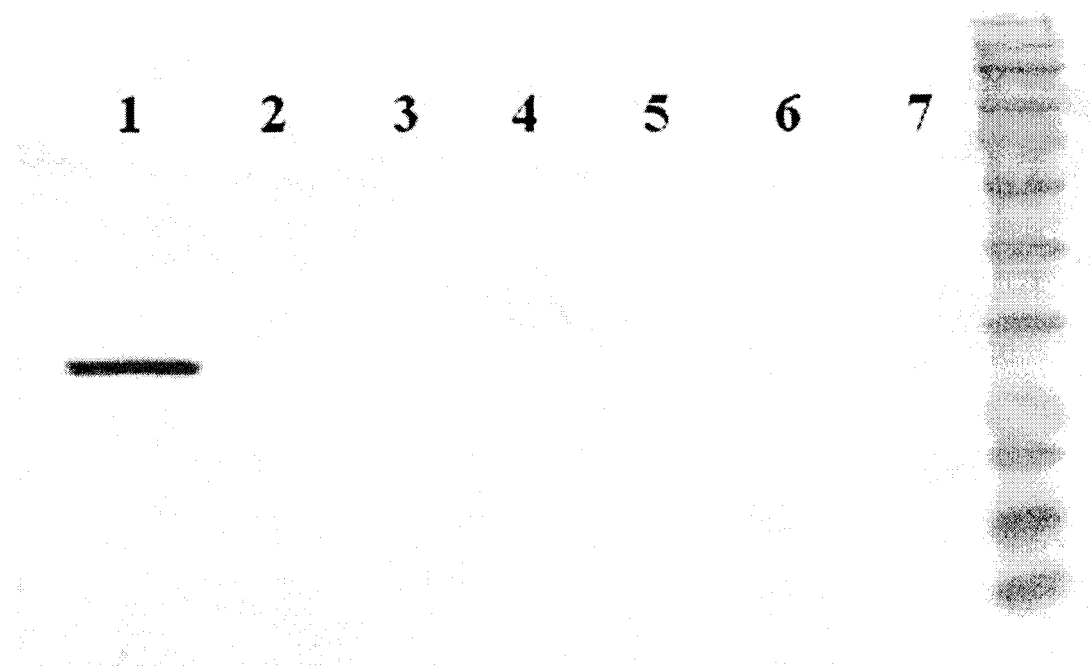
FIG. 15 shows monoclonal antibody specificity. Lane (1): JP728 (NetE+); Lane (2): NCTC3110 (Type B); Lane (3): NCTC7368 (Type B); Lane (4): ATCC3628 (Type C); Lane (5): NCTC3181 (Type C); Lane (6): CP4 (NetB+); Lane (7): CP1 (NetB+). Monoclonal antibody is specific for NetE. No Cross-reaction with other major C. perfringens toxins.

Specificity of Polyclonal and Monoclonal Antibodies:

To determine the specificity of antibodies, Western blot of culture supernatants of two type B, two type C and two netB-positive strains was performed using mouse and rabbit antisera against rNetE. As shown in FIGS. 14 and 15, the monoclonal antibody was found to be specific for NetE but the polyclonal antibody cross-reacted weakly with NetB but not with the beta toxin in type B or C strains.

Immunization of Horses with rNetE-NusA:

Horses were immunized with the rNetE-NusA protein. The antigen, which had not been inactivated to reduce toxicity, was found to be locally toxic, as outlined in Table 5.

NetE ELISA Antibody Responses of Horses to Immunization with rNetE-NusA:

The ELISA antibody response to NetE of 3 horses to immunization with rNetE-NusA is shown in Table 6. A difference in ELISA reactivity between horses is noteworthy, with the most responsive being the two horses with higher initial titers.

NetE Neutralizing Antibody Responses of Horses to Immunization with rNetE-NusA:

The cytotoxin neutralizing antibody response of 3 horses to immunization with rNetE-NusA is shown in Table 7. All horses developed increased neutralizing antibody titers following immunization. A difference in neutralizing ability between horses is noteworthy. Horse 1, which had the highest initial ELISA and neutralizing antibody titer, was the most responsive of the horses. Horse 2, which developed a very high ELISA antibody titer, showed a relatively poor neutralizing antibody response. There was no apparent relation between antibody response and local reaction to immunization.

Discussion

The demonstration of a novel pore-forming toxin designated NetE in type A *Clostridium perfringens* advances understanding of the role of this organism and its toxin in foal small bowel necrotizing enteritis and in canine hemorrhagic gastroenteritis, both of which are important but poorly understood diseases of economic and disease importance. This toxin gene has not previously been described. The present inventors have used a large collection of isolates of *C. perfringens* from the feces or intestine of healthy and diarrheic animals of different species to show the highly significant association of netE with the two important disease conditions of animals, specifically foal severe necrotizing enteritis and canine hemorrhagic gastroenteritis. The recognition that netE is on a plasmid may explain the lack of complete association to these two diseases, since it is well recognized that the large conjugative plasmids of *C. perfringens* can be lost on subculture.

There was a 100% association of netE-positive strains with presence of the cpe enterotoxin gene in cases of canine hemorrhagic gastroenteritis or foal severe small bowel necrotizing enteritis, although these two genes were shown to be on different plasmids. This association of these diseases with the two genes on their distinct plasmids is unlikely to occur by chance, and suggests that there may be a synergism between the two proteins or the two plasmids in the production of disease, or for some other reason. The netE gene is associated with isolates only from dogs and from horses, with the majority being associated with specific disease. The gene is highly conserved at the nucleotide level in isolates from dogs and horses. This does not preclude involvement of netE-positive *C. perfringens* with severe enteric disease in other species, since type A *C. perfringens* have been associated with hemorrhagic and necrotizing enteritis in a variety of other species (Songer, 1996).

All strains carrying the netE gene have marked cytotoxic activity against an equine ovarian cell line. The choice of this cell line to screen supernatants of isolates from horses with inflammation of the colon and of foals with necrotizing enteritis was because this is a cell line of equine origin. Canine-origin cell lines are the next most susceptible after the equine cell line. A visual assay was developed for toxicity and for the assessment of neutralizing antibody raised against the purified NetE protein.

In addition, a way to purify soluble NetE using a NusA fusion protein technology was developed, since recombinant NetE produced by more conventional his-tagged approaches in *E. coli* is insoluble. The *E. coli* host produces rNetE-NusA in large amounts. The pET 43.1a(NusA) vector was modified so as to produce purified soluble rNetE. However, the present inventors have found that immunization of horses with the rNetE-NusA fusion protein produces high antibody responses, as determined by ELISA. The protein also produces neutralizing antibody titers to the supernatant of netE-positive strains. There is a "discrepancy" between the high ELISA titers and the generally lower neutralizing antibody titers, which likely relate to the relative insensitivity of the visual cytotoxicity assay. There is variability in the immune response to NetE in horses immunized with the rNetE-NusA protein, which may relate to the prior existence of exposure to NetE ("immunological memory") in the immunized horse. The rNetE-NusA protein is locally very reactive in horses on intramuscular injection, so that the toxicity of the NetE protein needs to be inactivated by toxoiding in order to be used as an immunogen. The present inventors have shown that the rNetE protein can be used to produce polyclonal antibodies in rabbits that are also neutralizing. In addition, a monoclonal antibody produced against rNetE neutralized the toxicity of culture supernatants and was specific for the NetE protein; in contrast rabbit polyclonal antibody showed minor cross-reactivity with NetB, a toxin associated with necrotic enteritis of chickens.

Mares can be immunized with NetE or rNetE-NusA to provide lactogenic immunity in foals sucking on immunized mares, since mares have antibodies in their milk which should neutralize toxin produced in the small intestine by *C. perfringens*. The significance of this is that mare colostral antibodies often contain trypsin-inhibiting factors. Trypsin coming from the pancreas usually breaks down toxins produced by *C. perfringens* in the small intestine; colostrum can inhibit this process, explaining why this disease is seen especially in neonatal foals. The disease usually affects the small bowel of foals since native proteases produced by the large bowel microflora are likely to breakdown NetE produced in the large intestine. Having local antibody in colostrum that neutralizes the NetE toxin in the small intestine protects foals against this very serious and commonly fatal disease. There are currently commercially-available equine vaccines given to mares to protect their foals against viral enteritis.

Diagnosis and control of equine severe typhlocolitis can also be improved. This is a disease about which there is considerable uncertainty around diagnosis, treatment and control.

Further, diagnosis and control of canine hemorrhagic gastroenteritis can be improved. This is also a disease about which there is considerable uncertainty around diagnosis, treatment and control. The netE gene appears to be more common in canine diarrheal isolates than in equine diarrheal isolates generally. Accordingly, rapid diagnostic ELISA assays for tests on feces based on the monoclonal antibody are able to detect the presence of this toxin; Dogs are commonly immunized against viral enteric disease, and the present data demonstrates that they can be immunized against canine hemorrhagic gastroenteritis using viral-vectored recombinant and genetically toxoided NetE or rNetE-NusA.

The toxoided NetE protein may also be useful in immunization against a disease such as necrotic enteritis in chickens, since there is antigenic cross-reactivity with NetB, a toxin shown to be important in avian necrotic enteritis. There may be other applications to diagnosis, treatment and control in other animal species including humans should netE-positive *C. perfringens* be shown to be involved in serious enteric disease in these species.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Primers

| Primer names | 5'-3' | PCR size (bp) | References | SEQ ID NO: |
|---|---|---|---|---|
| PCR | | | | |
| netE-F | AATTCAGTATATTCACATGCAG | 1026 | | 4 |
| netE-R | CAGTTATACCGATTGTATTAGA | | | 3 |
| alpha-toxin-F | GCTAATGTTACTGCCGTTGA | 325 | Nowell et | 6 |
| alpha-toxin-R | CCTCTGATACATCGTGTAAG | | al., 2010 | 7 |
| beta2-F | ATTATGTTTAGGAATACAGTTA | 741 | Jost et | 8 |
| beta2-R | CAATACCCTTCACCAAATACTC | | al., 2005 | 9 |
| enterotoxin-F | GGAGATGGTTGGATATTAGG | 223 | | 10 |
| enterotoxin-R | GGACCAGCAGTTGTAGATA | | | 11 |
| Southern blot probes | | | | |
| NetEprobe-F | CCTTCAACAGATATATTTCCTCCAA | 419 | | 12 |
| NetEprobe-R | ACACAAACTCAAGTGTTTGCAAGT | | | 13 |
| Cpeprobe-F | GGAGATGGTTGGATATTAGG | 223 | Nowell et | 14 |
| Cpeprobe-R | GGACCAGCAGTTGTAGATA | | al., 2010 | 15 |
| Recombinant Protein | | | | |
| RecNetE-F | CCGCGAATTCTCTACTAGTTTAGCT CTTGCAAG | 957 | | 16 |
| RecNetE-R | CCGCAAGCTTTAGAAAACGTTCAAT TGTATGG | | | 17 |
| mRecNetE-F | CGGCGAATTCAGTGAATTAGGCAAT ACTAAGA | 888 | | 18 |
| mRecNetE-R | CGGCAAGCTTTAGAAAACGTTCAAT TGTATGG | | | 19 |

TABLE 2

Equine ovarian cell line cytotoxicity of supernatant of an equine foal necrotizing enteritis isolate JP728 (netE-positive strain) in comparison with CPB (beta toxin), CPE (enterotoxin) and CPB2 (atypical beta2 toxin) controls. Toxicity end-points are shown in bold and underlining.

| Isolate | 1:2 | 1:4 | 1:8 | 1:16 | 1:32 | 1:64 | 1:128 | 1:256 | 1:512 |
|---|---|---|---|---|---|---|---|---|---|
| NCTC3110 (CPB+) | 4+ | 4+ | 4+ | 2+ | N | N | N | N | N |
| JP564 (CPE+/CPB2+) | 4+ | 4+ | 3+ | N | N | N | N | N | N |
| SM101 (CPE+) | 4+ | 2+ | N | N | N | N | N | N | N |
| JP728 (NetE+) | 4+ | 4+ | 4+ | 4+ | 4+ | 2+ | N | N | N |
| CW504 (CPA+) | N | N | N | N | N | N | N | N | N |
| TPG media | N | N | N | N | N | N | N | N | N |

TABLE 3

Sequence of netE gene, NetE protein and the recombinant NetE protein fused with NusA and nucleic acid encoding said fusion.

netE gene (SEQ ID NO: 1)
```
ATGTCTACTAGTTTAGCTCTTGCAAGTATTGTTAGTACAAGTATTTTTTCAACACAAAC
TCAAGTGTTTGCAAGTGAATTAGGCAATACTAAGAAAATAGAGCTGAAAAATCAAA
TGGAGAAATAATAAAAGAAGATGGAAAGGAAGCTATTAAATACACTTCTATTGATAC
TTCTTCATGTAAAGGGTTAAAAGCAACATTAAGTGGAACTTTTGTTGAAGATCAATAT
TCTGATAAGAAAACTGCTTTACTAAATTTAGATGGGTTTATACCTTCAGGTAAGAAAG
TATCTGGTTCTACATATTGGAAAGATGAAGTGGCCTGAAGTTTATAGAATTAGTAT
AGAAAGCGCTGATACAGCTAATAAAGTAAAAATAGCAAATTCTATACCTAAAAATAC
TATAGATAAAAGGAGGTATCTAATTCAATTGGATATTCAATTGGAGGAAATATATCT
GTTGAAGGTAAAAGTGGTAGTGCAGGAATAAATGCTTCATACAGTGTACAAAATACT
ATAAGCTATGAACAACCTGATTTTAGAACAATCCAAAGAAAAGATGAAGAAAAGTTA
GCTTCATGGGATATAAAATTTGTTGAAACTAAAGATGGTTATAATCTGGATTCATATC
ATGGTATTTATGGGAATCAATTATTTATGAAATCAAGATTATATAATAATGGTTATGA
AAACTTTACTGATGATAGAGATCTCTCAACTTTAATTTCAGGTGGCTTTTCACCTAATA
TGGCAGTAGCTTTAACAGCGCCAAAAGATGCTAAAGAATCTATGATAACAGTTACAT
ATAAAAGATTTGACGATGAGTATACTTTGAATTGGGAAACTACTCAATGGAGGGGAT
CAAATAAACGTTCAACTGCATGTGAATATACTGAATTTATGTTTAAAATTAATTGGGA
AAACCATACAATTGAACGTTTTCTATAA
```

NetE protein (SEQ ID NO: 2)
```
MSTSLALASIVSTSIFSTQTQVFASELGNTKKIELKNQNGEIIKEDGKEAIKYTSIDTSSCKGL
KATLSGTFVEDQYSDKKTALLNLDGFIPSGKKVSGSTYYGKMKWPEVYRISIESADTANKV
KIANSIPKNTIDKKEVSNSIGYSIGGNISVEGKSGSAGINASYSVQNTISYEQPDFRTIQRKD
EEKLASWDIKFVETKDGYNLDSYHGIYGNQLFMKSRLYNNGYENFTDDRDLSTLISGGFS
PNMAVALTAPKDAKESMITVTYKRFDDEYTLNWETTQWRGSNKRSTACEYTEFMFKIN
WENHTIERFL
``` rNetE::NusA protein (SEQ ID NO: 5)
```
MNKEILAVVEAVSNEKALPREKIFEALESALATATKKKYEQEIDVRVQIDRKSGDFDTFRR
WLVVDEVTQPTKEITLEAARYEDESLNLGDYVEDQIESVTFDRITTQTAKQVIVQKVREAE
RAMVVDQFREHEGEIITGVVKKVNRDNISLDLGNNAEAVILREDMLPRENFRPGDRVRG
VLYSVRPEARGAQLFVTRSKPEMLIELFRIEVPEIGEEVIEIKAAARDPGSRAKIAVKTNDKR
IDPVGACVGMRGARVQAVSTELGGERIDIVLWDDNPAQFVINAMAPADVASIVVDEDK
HTMDIAVEAGNLAQAIGRNGQNVRLASQLSGWELNVMTVDDLQAKHQAEAHAAIDTF
TKYLDIDEDFATVLVEEGFSTLEELAYVPMKELLEIEGLDEPTVEALRERAKNALATIAQAQ
EESLGDNKPADDLLNLEGVDRDLAFKLAARGVCTLEDLAEQGIDDLADIEGLTDEKAGALI
MAARNICWFGDEATSRGSAGSGTIDDDDKSPGARGSEF**SELGNTKKIELKNQNGEIIKED
GKEAIKYTSIDTSSCKGLKATLSGTFVEDQYSDKKTALLNLDGFIPSGKKVSGSTYYGKMK
WPEVYRISIESADTANKVKIANSIPKNTIDKKEVSNSIGYSIGGNISVEGKSGSAGINASYSV
QNTISYEQPDFRTIQRKDEEKLASWDIKFVETKDGYNLDSYHGIYGNQLFMKSRLYNNGY
ENFTDDRDLSTLISGGFSPNMAVALTAPKDAKESMITVTYKRFDDEYTLNWETTQWRGS
NKRSTACEYTEFMFKINWENHTIERFLKLAAAQLYTRASQPELAPEDPEDL**HHHHHHX
``` rNetE::NusA nucleic acid (SEQ ID NO: 24)
```
ATGAACAAAGAAATTTTGGCTGTAGTTGAAGCCGTATCCAATGAAAAGGCGCTACCT
CGCGAGAAGATTTTCGAAGCATTGGAAAGCGCGCTGGCGACAGCAACAAAGAAAAA
ATATGAACAAGAGATCGACGTCCGCGTACAGATCGATCGCAAAAGCGGTGATTTTGA
CACTTTCCGTCGCTGGTTAGTTGTTGATGAAGTCACCCAGCCGACCAAGGAAATCACC
CTTGAAGCCGCACGTTATGAAGATGAAAGCCTGAACCTGGGCGATTACGTTGAAGAT
CAGATTGAGTCTGTTACCTTTGACCGTATCACTACCCAGACGGCAAAACAGGTTATCG
TGCAGAAAGTGCGTGAAGCCGAACGTGCGATGGTGGTTGATCAGTTCCGTGAACAC
GAAGGTGAAATCATCACCGGCGTGGTGAAAAAAGTAAACCGCGACAACATCTCTCTG
GATCTGGGCAACAACGCTGAAGCCGTGATCCTGCGCGAAGATATGCTGCCGCGTGA
AAACTTCCGCCCTGGCGACCGCGTTCGTGGCGTGCTCTATTCCGTTCGCCCGGAAGC
GCGTGGCGCGCAACTGTTCGTCACTCGTTCCAAGCCGGAAATGCTGATCGAACTGTT
CCGTATTGAAGTGCCAGAAATCGGCGAAGAAGTGATTGAAATTAAAGCAGCGGCTC
GCGATCCGGGTTCTCGTGCGAAAATCGCGGTGAAAACCAACGATAAACGTATCGATC
CGGTAGGTGCTTGCGTAGGTATGCGTGGCGCGCGTGTTCAGGCGGTGTCTACTGAA
CTGGGTGGCGAGCGTATCGATATCGTCCTGTGGGATGATAACCCGGCGCAGTTCGTG
ATTAACGCAATGGCACCGGCAGACGTTGCTTCTATCGTGGTGGATGAAGATAAACAC
ACCATGGACATCGCCGTTGAAGCCGGTAATCTGGCGCAGGCGATTGGCCGTAACGG
TCAGAACGTGCGTCTGGCTTCGCAACTGAGCGGTTGGGAACTCAACGTGATGACCGT
TGACGACCTGCAAGCTAAGCATCAGGCGGAAGCGCACGCAGCGATCGACACCTTCA
```

TABLE 3-continued

Sequence of netE gene, NetE protein and the recombinant NetE protein fused with NusA and nucleic acid encoding said fusion.

<u>CCAAATATCTCGACATCGACGAAGACTTCGCGACTGTTCTGTAGAAGAAGGCTTCT
CGACGCTGGAAGAATTGGCCTATGTGCCGATGAAAGAGCTGTTGGAAATCGAAGGC
CTTGATGAGCCGACCGTTGAAGCACTGCGCGAGCGTGCTAAAAATGCACTGGCCACC
ATTGCACAGGCCCAGGAAGAAAGCCTCGGTGATAACAAACCGGCTGACGATCTGCT
GAACCTTGAAGGGGTAGATCGTGATTTGGCATTCAAACTGGCCGCCCGTGGCGTTTG
TACGCTGGAAGATCTCGCCGAACAGGGCATTGATGATCTGGCTGATATCGAAGGGTT
GACCGACGAAAAAGCCGGAGCACTGATTATGGCTGCCCGTAATATTTGCTGGTTCGG
TGACGAAGCG</u> *ACTAGG* <u>CCGGGGCAGCGCGGGTTCTGGTACGATT**GATGACGACGA
CAAGAGTCCGGGAGCTCGTGGATCCGAATTC**AGTGAATTAGGCAATACTAAGAAAA
TAGAGCTGAAAAATCAAAATGGAGAAATAATAAAAGAAGATGGAAAGGAAGCTATT
AAATACACTTCTATTGATACTTCTTCATGTAAAGGGTTAAAAGCAACATTAAGTGGAA
CTTTTGTTGAAGATCAATATTCTGATAAGAAAACTGCTTTACTAAATTTAGATGGGTTT
ATACCTTCAGGTAAGAAAGTATCTGGTTCTACATATTATGGAAAGATGAAGTGGCCT
GAAGTTTATAGAATTAGTATAGAAAGCGCTGATACAGCTAATAAAGTAAAAATAGCA
AATTCTATACCTAAAAATACTATAGATAAAAAGGAGGTATCTAATTCAATTGGATATT
CAATTGGAGGAAATATATCTGTTGAAGGTAAAAGTGGTAGTGCAGGAATAAATGCTT
CATACAGTGTACAAAATACTATAAGCTATGAACAACCTGATTTTAGAACAATCCAAAG
AAAAGATGAAGAAAAGTTAGCTTCATGGGATATAAAATTTGTTGAAACTAAAGATGG
TTATAATCTGGATTCATATCATGGTATTTATGGGAATCAATTATTTATGAAATCAAGAT
TATATAATAATGGTTATGAAAACYYYACTGATGATAGAGATCTCTCAACTTTAATTTCA
GGTGGCTTTTCACCTAATATGGCAGTAGCTTTAACAGCGCCAAAAGATGCTAAAGAA
TCTATGATAACAGTTACATATAAAAGATTTGACGATGAGTATACTTTGAATTGGGAAA
CTACTCAATGGAGGGGATCAAATAAACGTTCAACTGCATGTGAATATACTGAATTTAT
GTTTAAAATTAATTGGGAAAACCATACAATTGAACGTTTTCTAAAGCTTGCGGCCGCA
CAGCTGTATACACGTGCAAGCCAGCCAGAACTCGCTCCTGAAGACCCAGAGGATCTC
GAG</u><u>CACCACCACCACCACCACTAA</u>

<u>NusA</u>: heterologous protein to enhance solubility;
<u>NetE</u>: target protein, Enterokinase site: DDDKSP for cleavage of rNetE::NusA, Histidine tag:
HHHHHH for purification of rNetE.

TABLE 4

Host cell cytotoxicity specificity of supernatant from netE and cph-positive *C. perfringens*

| Name of cell line | Species | NCTC3110 Toxicity dilution | J

TABLE 6

ELISA titers to rNetE in 3 adult horses

| Horses | Time (Days) | | | | |
|---|---|---|---|---|---|
| | 0 | 14 | 28 | 35 | 42 |
| 1 | 3200 | 12800 | 204800 | ≥409600 | ≥409600 |
| 2 | 1600 | 3200 | 204800 | ≥409600 | ≥409600 |
| 3 | 800 | 3200 | 12800 | 25600 | 25600 |

TABLE 7

Neutralizing antibody titers to rNetE in 3 adult horses.

| Horses | Time (Days) | | | | |
|---|---|---|---|---|---|
| | 0 | 14 | 28 | 35 | 42 |
| 1 | 128 | 16384 | 32768 | 65536 | 65536 |
| 2 | No Neutralization | No Neutralization | 8 | 32 | 64 |
| 3 | No Neutralization | 2 | 64 | 128 | 128 |

REFERENCES

Chan C, Farzan A, Soltes G, Nicholson V M, Pei Y, et al. (2012) The epidemiology of *Clostridium perfringens* type A on Ontario swine farms, with special reference to cpb2-positive isolates. BMC Vet Res 8: 156.

Diab S S, Kinde H, Moore J, Shahriar M F, et al. (2012) Pathology of *Clostridium perfringens* Type A enterotoxemia in horses. Vet Path 49: 255-263.

East L M, Savage C J, Traub-Dargatz J L, Dickinson C E, Ellis R P. (1998) Enterocolitis associated with *Clostridium perfringens* infection in neonatal foals: 54 cases (1988-1997). J Am Vet Med Assoc 212: 1751-1756.

East L M, Dargatz D A, Traub-Dargatz J L, Savage C J. 2000. Foaling-management practices associated with the occurrence of enterocolitis attributed to *Clostridium perfringens* infection in the equine neonate. Prev Vet med 46: 61-74.

Farzan A, Kircanski J, DeLay J, Soltes G, Songer J G, et al. (2013) An investigation into the association between cpb2-encoding *Clostridium perfringens* type A and diarrhea in neonatal piglets. Can J Vet Res 77: 45-53.

Gobeli S, Berset C, Burgener I A, Perreten V. ((2012) Antimicrobial susceptibility of canine *Clostridium perfringens* strains from Switzerland. Schweiz Archiv Tierheil 154: 254-250.

Hazlett M J, Kircansji J, Slavic S. Prescott J F. (2011) Beta2 toxigenic *Clostridium perfringens* type A colitis in a three-day-old foal. J Vet Diag Invest 23:373-376.

Jost B H, Billington S J, Trinh H T, Bueschel D M, Songer J G. (2005) Atypical cpb2 genes, encoding beta2-toxin in *Clostridium perfringens* isolates of non-porcine origin. Infect Immun. 73:652-656.

Kanoe M, Inoue S, Abe T, Anzai T, Kamada M, et al. (1990). Isolation of *Clostridium perfringens* from foals. Microbios 64: 153-158.

Keyburn A L, Boyce J D, Vaz P, Bannam T L, Ford M E, et al. (2008) NetB, a new toxin that is associated with avian necrotic enteritis caused by *Clostridum perfringens*. PLoS Pathogens 4:e26.

Kircanski J, Parreira V R, Whiteside S, Pei Y, Prescott J F (2012a) The majority of atypical cpb2 genes in *Clostridium perfringens* isolates of different domestic animal origin are expressed. Vet Microbiol 159: 371-374.

Kircanski J, Hodgins D, Soltes G, Pei Y, Parreira V R, et al. (2012b) Development of an antigen-capture enzyme-linked immunosorbent assay for *Clostridium perfringens* beta2-toxin in porcine feces and the neonatal piglet intestine. J Vet Diagn Invest 24:895-902.

Lepp D, Roxas B, Parreira V R, Marri P R, Rosey E L, et al. (2010) Identification of novel pathogenicity loci in *Clostridium perfringens* strains that cause avian necrotic enteritis. PLoS One 5:e10795.

Marks S L. (2012) *Clostridium perfringens*- and *Clostridium difficile*-associated diarrhea. In: Greene C E, editor. Infectious Diseases of the Dog and Cat, 4th ed. St. Louis: Saunders Elsevier, pp. 395-395; 974.

McClung L S (1945) Human food poisoning due to growth of *Clostridium perfringens* (*C. welchii*) in freshly cooked chicken: preliminary note. J. Bacteriol. 50:229-231.

Mehdizadeh Gohari I, Arroyo L, Machines J I, Timoney J F, Parreira V R, et al. (2013) Characterization of *Clostridium perfringens* in the feces of adult horses and foals with acute diarrhea. Can J Vet Res (in press).

Netherwood T, Wood J L N, Mumford J A, Chanter N. (1998) Molecular analysis of the virulence determinants of *Clostridium perfringens* associated with foal diarrhea. Vet J 155: 289-294.

Nowell V, Poppe C, Parreira V R, Jiang Y, Reid-Smith R, et al (2010) *Clostridium perfringens* in retail chicken. Anaerobe 16: 314-315.

Parreira V R., Costa M, Eikmeyer F, Blom J, Prescott J F (2012) Sequence of two plasmids from *Clostridium perfringens* chicken necrotic enteritis isolates and comparison with *C. perfringens* conjugative plasmids. PLoS One 7: e49753.

Pospiech A, Neumann B. (1995) A versatile quick-prep of genomic DNA from gram-positive bacteria. Trends Genet 11: 217-218.

Potter K, 2011. Case #28. Am Coll Vet Pathologists Annual Meeting.

Prescott J F, Johnson J A, Patterson J M, and Bulmer W S. (1978) Haemorrhagic gastroenteritis in the dog associated with *Clostridium welchii*. Vet Rec 103: 116-117.

Roth F, Jansen K, Petzke S. (1999) Detection of neutralizing antibodies against alpha-toxin of different *Clostridium septicum* strains in cell culture. FEMS Immunol Med Microbiol 24:353-359.

Ruby R, Magdesian G, Kass P H. (2009) Comparison of clinical, microbiologic, and clinicopathologic findings in horses positive and negative for *Clostridium difficile* infection. J Am Vet Med Assoc 234: 777-784.

Sasaki J, Goryo M, Asahina M, Makara M, Shisido S, et al. (1999) Hemorrhagic enteritis associated with *Clostridium perfringens* type A in a dog. J Vet Med Sci 61: 175-177.

Schlegel B, Van Dreumel T, Slavic D, Prescott J F. (2012a) *Clostridium perfringens* type A fatal acute hemorrhagic gastroenteritis in a dog. Can Vet J 53: 555-558.

Schlegel B J, Nowell V J, Parreira V R, Soltes G, Prescott J F (2012b) Toxin-associated and other genes in type A *Clostridium perfringens* isolates from bovine clostridial abomasitis and jejunal hemorrhage syndrome. Can J Vet Res 76: 248-254.

Songer J G. 1996. Clostridial enteric diseases of domestic animals. Clin Microbiol Rev 9:216-234.

Timoney J F, Hartmann M. Fallon L, Fallon E, Walker J. (2005) Antibody responses of mares to prepartum vaccination with *Clostridium perfringens* bacterin and beta2 toxin. Vet Rec 157:810-812.

Traub-Dargatz J L, Jones R L. 1993. Clostridia-associated enterocolitis in adult horses and foals. Vet Clin North Am 9: 411-421.

The invention claimed is:

1. An isolated polypeptide encoded by a nucleic acid molecule comprising the nucleic acid sequence as shown in SEQ ID NO:1 or a variant thereof that encodes a protein having at least 90% identity to the full length protein encoded by SEQ ID NO:1 or comprising the amino acid sequence as shown in SEQ ID NO:2 or a variant thereof having at least 90% sequence identity to the full length protein as shown in SEQ ID NO:2, wherein the polypeptide is toxoided.

2. An isolated fusion protein comprising a polypeptide encoded by a nucleic acid molecule comprising the nucleic acid sequence as shown in SEQ ID NO:1 or a variant thereof that encodes a protein having at least 90% identity to the full length protein encoded by SEQ ID NO:1 or comprising the amino acid sequence as shown in SEQ ID NO:2 or a variant thereof having at least 90% sequence identity to the full length protein as shown in SEQ ID NO:2; fused to a solubility protein.

3. The isolated fusion protein of claim 2, wherein the solubility protein is NusA.

4. An immunogenic composition comprising supernatant isolated from a NetE-positive *C. perfringens* strain; wherein NetE is encoded by the nucleic acid sequence as shown in SEQ ID NO:1 or a variant thereof that encodes a protein having at least 90% sequence identity to the full length protein encoded by SEQ ID NO:1; and further comprising an immunostimulatory amount of an adjuvant.

5. The immunogenic composition of claim 4, wherein the supernatant is concentrated.

6. The immunogenic composition of claim 4, further comprising additional isolated NetE protein or NetE-solubility fusion protein.

7. The immunogenic composition of claim 4, further comprising an additional *C. perfringens* toxin protein, wherein the additional *C. perfringens* toxin protein is Cpe, Cpa, NetB, Cpb2 or TpeL.

8. An immunogenic composition comprising the isolated polypeptide of claim 1 and an immunostimulatory amount of an adjuvant.

9. An immunogenic composition comprising the isolated fusion protein of claim 2 and an immunostimulatory amount of an adjuvant.

10. An immunogenic composition comprising an isolated polypeptide encoded by a nucleic acid molecule comprising the nucleic acid sequence as shown in SEQ ID NO:1 or a variant thereof that encodes a protein having at least 90% identity to the full length protein encoded by SEQ ID NO:1 or comprising the amino acid sequence as shown in SEQ ID NO:2 or a variant thereof having at least 90% sequence identity to the full length protein as shown in SEQ ID NO:2, and further comprising an immunostimulatory amount of an adjuvant.

* * * * *

SEQUENCE LISTING

<160> NUMBER OF SEQ ID NOS: 24

<210> SEQ ID NO 1
<211> LENGTH: 951
<212> TYPE: DNA
<213> ORGANISM: Clostridium perfringens

<400> SEQUENCE: 1

```
atgtctacta gtttagctct tgcaagtatt gttagtacaa gtattttttc aacacaaact      60
caagtgtttg caagtgaatt aggcaatact aagaaaatag agctgaaaaa tcaaaatgga     120
gaaataataa agaagatgg aaaggaagct attaaataca cttctattga tacttcttca     180
tgtaaagggt taaagcaac attaagtgga actttgttg aagatcaata ttctgataag     240
aaaactgctt tactaaattt agatgggttt ataccttcag gtaagaaagt atctggttct     300
acatattatg aaagatgaa gtggcctgaa gtttatagaa ttagtataga aagcgctgat     360
acagctaata agtaaaaat agcaaattct atacctaaaa atactataga taaaaaggag     420
gtatctaatt caattggata ttcaattgga ggaaatatat ctgttgaagg taaaagtggt     480
agtgcaggaa taaatgcttc atacagtgta caaaatacta taagctatga caacctgat     540
tttagaacaa tccaaagaaa agatgaagaa aagttagctt catgggatat aaaatttgtt     600
gaaactaaag atggttataa tctggattca tatcatggta tttatgggaa tcaattattt     660
atgaaatcaa gattatataa taatggttat gaaaactta ctgatgatag agatctctca     720
actttaattt caggtggctt ttcacctaat atggcagtag ctttaacagc gccaaaagat     780
gctaaagaat ctatgataac agttacatat aaaagatttg acgatgagta tactttgaat     840
tgggaaacta ctcaatggag gggatcaaat aaacgttcaa ctgcatgtga atatactgaa     900
tttatgttta aaattaattg ggaaaaccat acaattgaac gttttctata a              951
```

<210> SEQ ID NO 2
<211> LENGTH: 316
<212> TYPE: PRT
<213> ORGANISM: Clostridium perfringens

<400> SEQUENCE: 2

```
Met Ser Thr Ser Leu Ala Leu Ala Ser Ile Val Ser Thr Ser Ile Phe
1               5                   10                  15

Ser Thr Gln Thr Gln Val Phe Ala Ser Glu Leu Gly Asn Thr Lys Lys
            20                  25                  30

Ile Glu Leu Lys Asn Gln Asn Gly Glu Ile Ile Lys Glu Asp Gly Lys
        35                  40                  45

Glu Ala Ile Lys Tyr Thr Ser Ile Asp Thr Ser Ser Cys Lys Gly Leu
    50                  55                  60

Lys Ala Thr Leu Ser Gly Thr Phe Val Glu Asp Gln Tyr Ser Asp Lys
65                  70                  75                  80

Lys Thr Ala Leu Leu Asn Leu Asp Gly Phe Ile Pro Ser Gly Lys Lys
                85                  90                  95

Val Ser Gly Ser Thr Tyr Tyr Gly Lys Met Lys Trp Pro Glu Val Tyr
            100                 105                 110

Arg Ile Ser Ile Glu Ser Ala Asp Thr Ala Asn Lys Val Lys Ile Ala
        115                 120                 125

Asn Ser Ile Pro Lys Asn Thr Ile Asp Lys Lys Glu Val Ser Asn Ser
    130                 135                 140

Ile Gly Tyr Ser Ile Gly Gly Asn Ile Ser Val Glu Gly Lys Ser Gly
145                 150                 155                 160
```

```
Ser Ala Gly Ile Asn Ala Ser Tyr Ser Val Gln Asn Thr Ile Ser Tyr
                165                 170                 175

Glu Gln Pro Asp Phe Arg Thr Ile Gln Arg Lys Asp Glu Glu Lys Leu
            180                 185                 190

Ala Ser Trp Asp Ile Lys Phe Val Thr Lys Asp Gly Tyr Asn Leu
        195                 200                 205

Asp Ser Tyr His Gly Ile Tyr Gly Asn Gln Leu Phe Met Lys Ser Arg
    210                 215                 220

Leu Tyr Asn Asn Gly Tyr Glu Asn Phe Thr Asp Asp Arg Asp Leu Ser
225                 230                 235                 240

Thr Leu Ile Ser Gly Gly Phe Ser Pro Asn Met Ala Val Ala Leu Thr
                245                 250                 255

Ala Pro Lys Asp Ala Lys Glu Ser Met Ile Thr Val Thr Tyr Lys Arg
            260                 265                 270

Phe Asp Asp Glu Tyr Thr Leu Asn Trp Glu Thr Thr Gln Trp Arg Gly
        275                 280                 285

Ser Asn Lys Arg Ser Thr Ala Cys Glu Tyr Thr Glu Phe Met Phe Lys
    290                 295                 300

Ile Asn Trp Glu Asn His Thr Ile Glu Arg Phe Leu
305                 310                 315

<210> SEQ ID NO 3
<211> LENGTH: 22
<212> TYPE: DNA
<213> ORGANISM: Clostridium perfringens

<400> SEQUENCE: 3
cagttatacc gattgtatta ga                                             22

<210> SEQ ID NO 4
<211> LENGTH: 22
<212> TYPE: DNA
<213> ORGANISM: Clostridium perfringens

<400> SEQUENCE: 4
aattcagtat attcacatgc ag                                             22

<210> SEQ ID NO 5
<211> LENGTH: 844
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (844)..(844)
<223> OTHER INFORMATION: Xaa can be any naturally occurring amino acid

<400> SEQUENCE: 5

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80
```

```
Arg Tyr Glu Asp Glu Ser Leu Asn Leu Gly Asp Tyr Val Glu Asp Gln
                    85                  90                  95

Ile Glu Ser Val Thr Phe Asp Arg Ile Thr Thr Gln Thr Ala Lys Gln
                100                 105                 110

Val Ile Val Gln Lys Val Arg Glu Ala Glu Arg Ala Met Val Val Asp
            115                 120                 125

Gln Phe Arg Glu His Glu Gly Glu Ile Ile Thr Gly Val Val Lys Lys
130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
                180                 185                 190

Ala Gln Leu Phe Val Thr Arg Ser Lys Pro Glu Met Leu Ile Glu Leu
            195                 200                 205

Phe Arg Ile Glu Val Pro Glu Ile Gly Glu Glu Val Ile Glu Ile Lys
210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
                260                 265                 270

Ile Val Leu Trp Asp Asp Asn Pro Ala Gln Phe Val Ile Asn Ala Met
            275                 280                 285

Ala Pro Ala Asp Val Ala Ser Ile Val Val Asp Glu Asp Lys His Thr
290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
                340                 345                 350

His Ala Ala Ile Asp Thr Phe Thr Lys Tyr Leu Asp Ile Asp Glu Asp
            355                 360                 365

Phe Ala Thr Val Leu Val Glu Glu Gly Phe Ser Thr Leu Glu Glu Leu
370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
                420                 425                 430

Asp Leu Leu Asn Leu Glu Gly Val Asp Arg Asp Leu Ala Phe Lys Leu
            435                 440                 445

Ala Ala Arg Gly Val Cys Thr Leu Glu Asp Leu Ala Glu Gln Gly Ile
450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Thr
                485                 490                 495
```

-continued

Ser Arg Gly Ser Ala Gly Ser Gly Thr Ile Asp Asp Asp Lys Ser
              500                 505                 510

Pro Gly Ala Arg Gly Ser Glu Phe Ser Glu Leu Gly Asn Thr Lys Lys
        515                 520                 525

Ile Glu Leu Lys Asn Gln Asn Gly Glu Ile Ile Lys Glu Asp Gly Lys
    530                 535                 540

Glu Ala Ile Lys Tyr Thr Ser Ile Asp Thr Ser Ser Cys Lys Gly Leu
545                 550                 555                 560

Lys Ala Thr Leu Ser Gly Thr Phe Val Glu Asp Gln Tyr Ser Asp Lys
                565                 570                 575

Lys Thr Ala Leu Leu Asn Leu Asp Gly Phe Ile Pro Ser Gly Lys Lys
            580                 585                 590

Val Ser Gly Ser Thr Tyr Tyr Gly Lys Met Lys Trp Pro Glu Val Tyr
        595                 600                 605

Arg Ile Ser Ile Glu Ser Ala Asp Thr Ala Asn Lys Val Lys Ile Ala
    610                 615                 620

Asn Ser Ile Pro Lys Asn Thr Ile Asp Lys Lys Glu Val Ser Asn Ser
625                 630                 635                 640

Ile Gly Tyr Ser Ile Gly Gly Asn Ile Ser Val Glu Gly Lys Ser Gly
                645                 650                 655

Ser Ala Gly Ile Asn Ala Ser Tyr Ser Val Gln Asn Thr Ile Ser Tyr
            660                 665                 670

Glu Gln Pro Asp Phe Arg Thr Ile Gln Arg Lys Asp Glu Lys Leu
        675                 680                 685

Ala Ser Trp Asp Ile Lys Phe Val Glu Thr Lys Asp Gly Tyr Asn Leu
    690                 695                 700

Asp Ser Tyr His Gly Ile Tyr Gly Asn Gln Leu Phe Met Lys Ser Arg
705                 710                 715                 720

Leu Tyr Asn Asn Gly Tyr Glu Asn Phe Thr Asp Asp Arg Asp Leu Ser
                725                 730                 735

Thr Leu Ile Ser Gly Gly Phe Ser Pro Asn Met Ala Val Ala Leu Thr
            740                 745                 750

Ala Pro Lys Asp Ala Lys Glu Ser Met Ile Thr Val Thr Tyr Lys Arg
        755                 760                 765

Phe Asp Asp Glu Tyr Thr Leu Asn Trp Glu Thr Thr Gln Trp Arg Gly
770                 775                 780

Ser Asn Lys Arg Ser Thr Ala Cys Glu Tyr Thr Glu Phe Met Phe Lys
785                 790                 795                 800

Ile Asn Trp Glu Asn His Thr Ile Glu Arg Phe Leu Lys Leu Ala Ala
                805                 810                 815

Ala Gln Leu Tyr Thr Arg Ala Ser Gln Pro Glu Leu Ala Pro Glu Asp
            820                 825                 830

Pro Glu Asp Leu Glu His His His His His Xaa
        835                 840

<210> SEQ ID NO 6
<211> LENGTH: 20
<212> TYPE: DNA
<213> ORGANISM: Clostridium perfringens

<400> SEQUENCE: 6
gctaatgtta ctgccgttga                                          20

<210> SEQ ID NO 7
<211> LENGTH: 20

```
<212> TYPE: DNA
<213> ORGANISM: Clostridium perfringens

<400> SEQUENCE: 7
cctctgatac atcgtgtaag                                              20

<210> SEQ ID NO 8
<211> LENGTH: 22
<212> TYPE: DNA
<213> ORGANISM: Clostridium perfringens

<400> SEQUENCE: 8
attatgttta ggaatacagt ta                                           22

<210> SEQ ID NO 9
<211> LENGTH: 22
<212> TYPE: DNA
<213> ORGANISM: Clostridium perfringens

<400> SEQUENCE: 9 caatacccttt caccaaatac tc                                          22

<210> SEQ ID NO 10
<211> LENGTH: 20
<212> TYPE: DNA
<213> ORGANISM: Clostridium perfringens

<400> SEQUENCE: 10
ggagatggtt ggatattagg                                              20

<210> SEQ ID NO 11
<211> LENGTH: 19
<212> TYPE: DNA
<213> ORGANISM: Clostridium perfringens

<400> SEQUENCE: 11
ggaccagcag ttgtagata                                               19

<210> SEQ ID NO 12
<211> LENGTH: 25
<212> TYPE: DNA
<213> ORGANISM: Clostridium perfringens

<400> SEQUENCE: 12
ccttcaacag atatatttcc tccaa                                        25

<210> SEQ ID NO 13
<211> LENGTH: 24
<212> TYPE: DNA
<213> ORGANISM: Clostridium perfringens

<400> SEQUENCE: 13
acacaaactc aagtgtttgc aagt                                         24

<210> SEQ ID NO 14
<211> LENGTH: 20
<212> TYPE: DNA
<213> ORGANISM: Clostridium perfringens

<400> SEQUENCE: 14
ggagatggtt ggatattagg                                              20

<210> SEQ ID NO 15
```

<211> LENGTH: 19
<212> TYPE: DNA
<213> ORGANISM: Clostridium perfringens

<400> SEQUENCE: 15
ggaccagcag ttgtagata 19

<210> SEQ ID NO 16
<211> LENGTH: 33
<212> TYPE: DNA
<213> ORGANISM: Artificial Sequence
<220> FEATURE:
<223> OTHER INFORMATION: Synthetic construct

<400> SEQUENCE: 16
ccgcgaattc tctactagtt tagctcttgc aag 33

<210> SEQ ID NO 17
<211> LENGTH: 32
<212> TYPE: DNA
<213> ORGANISM: Artificial Sequence
<220> FEATURE:
<223> OTHER INFORMATION: Synthetic construct

<400> SEQUENCE: 17
ccgcaagctt tagaaaacgt tcaattgtat gg 32

<210> SEQ ID NO 18
<211> LENGTH: 32
<212> TYPE: DNA
<213> ORGANISM: Artificial Sequence
<220> FEATURE:
<223> OTHER INFORMATION: Synthetic construct

<400> SEQUENCE: 18
cggcgaattc agtgaattag gcaatactaa ga 32

<210> SEQ ID NO 19
<211> LENGTH: 32
<212> TYPE: DNA
<213> ORGANISM: Artificial Sequence
<220> FEATURE:
<223> OTHER INFORMATION: Synthetic construct

<400> SEQUENCE: 19
cggcaagctt tagaaaacgt tcaattgtat gg 32

<210> SEQ ID NO 20
<211> LENGTH: 2115
<212> TYPE: DNA
<213> ORGANISM: Artificial Sequence
<220> FEATURE:
<223> OTHER INFORMATION: Synethic construct

<400> SEQUENCE: 20
agcaaccgca cctgtggcgc cggtgatgcc ggccacgatg cgtccggcgt agaggatcga 60
gatcgatctc gatcccgcga aattaatacg actcactata ggggaattgt gagcggataa 120
caattcccct ctagaaataa ttttgtttaa ctttaagaag gagatataca tatgaacaaa 180
gaaattttgg ctgtagttga agccgtatcc aatgaaaagg cgctacctcg cgagaagatt 240
ttcgaagcat tggaaagcgc gctggcgaca gcaacaaaga aaaaatatga acaagagatc 300
gacgtccgcg tacagatcga tcgcaaaagc ggtgattttg acactttccg tcgctggtta 360
gttgttgatg aagtcaccca gccgaccaag gaaatcaccc ttgaagccgc acgttatgaa 420

```
gatgaaagcc tgaacctggg cgattacgtt gaagatcaga ttgagtctgt tacctttgac    480
cgtatcacta cccagacggc aaaacaggtt atcgtgcaga aagtgcgtga agccgaacgt    540
gcgatggtgg ttgatcagtt ccgtgaacac gaaggtgaaa tcatcaccgg cgtggtgaaa    600
aaagtaaacc gcgacaacat ctctctggat ctgggcaaca acgctgaagc cgtgatcctg    660
cgcgaagata tgctgccgcg tgaaaacttc cgccctggcg accgcgttcg tggcgtgctc    720
tattccgttc gcccggaagc gcgtggcgcg caactgttcg tcactcgttc caagccggaa    780
atgctgatcg aactgttccg tattgaagtg ccagaaatcg gcgaagaagt gattgaaatt    840
aaagcagcgc tcgcgatccc gggttctcgt gcgaaaatcg cggtgaaaac caacgataaa    900
cgtatcgatc cggtaggtgc ttgcgtaggt atgcgtggcg cgcgtgttca ggcggtgtct    960
actgaactgg gtggcgagcg tatcgatatc gtcctgtggg atgataaccc ggcgcagttc   1020
gtgattaacg caatggcacc ggcagacgtt gcttctatcg tggtggatga agataaacac   1080
accatggaca tcgccgttga agccggtaat ctggcgcagg cgattggccg taacggtcag   1140
aacgtgcgtc tggcttcgca actgagcggt tgggaactca acgtgatgac cgttgacgac   1200
ctgcaagcta agcatcaggc ggaagcgcac gcagcgatcg acaccttcac caaatatctc   1260
gacatcgacg aagacttcgc gactgttctg gtagaagaag gcttctcgac gctggaagaa   1320
ttggcctatg tgccgatgaa agagctgttg gaaatcgaag ccttgatga gccgaccgtt    1380 gaagcactgc gcgagcgtgc taaaaatgca ctggccacca ttgcacaggc ccaggaagaa   1440
agcctcggtg ataacaaacc ggctgacgat ctgctgaacc ttgaaggggg agatcgtgat   1500
ttggcattca aactggccgc ccgtggcgtt tgtacgctgg aagatctcgc cgaacagggc   1560
attgatgatc tggctgatat cgaagggttg accgacgaaa aagccggagc actgattatg   1620
gctgcccgta atatttgctg gttcggtgac gaagcgacta gtggttctgg tcatcaccat   1680
caccatcact ccgcgggtaa agaaaccgct gctgcgaaat ttgaacgcca gcacatggac   1740
tcgccaccgc caactggtct ggtcccccgg ggcagcgcgg ttctggtac gattgatgac    1800 gacgacaaga gtccgggagc tcgtggatcc gaattctgta caggcgcgcc tgcaggacgt   1860
cgacggtacc atcgatacgc gttcgaagct tgcggccgca cagctgtata cacgtgcaag   1920
ccagccagaa ctcgctcctg aagacccaga ggatctcgag caccaccacc accaccacta   1980
atgttaatta agttgggcgt tcctaggctg ataaaacaga atttgcctgg cggcagtagc   2040
gcggtggtcc cacctgaccc catgccgaac tcagaagtga acgccgtag cgccgatggt    2100 agtgtggggt ctccc                                                    2115

<210> SEQ ID NO 21
<211> LENGTH: 2114
<212> TYPE: DNA
<213> ORGANISM: Artificial Sequence
<220> FEATURE:
<223> OTHER INFORMATION: Synthetic cosntruct

<400> SEQUENCE: 21
agcaaccgca cctgtggcgc cggtgatgcc ggccacgatg cgtccggcgt agaggatcga     60
gatcgatctc gatcccgcga aattaatacg actcactata ggggaattgt gagcggataa    120
caattcccct ctagaaataa ttttgtttaa ctttaagaag gagatataca tatgaacaaa    180
gaaattttgg ctgtagttga agccgtatcc aatgaaaagg cgctacctcg cgagaagatt    240
ttcgaagcat tggaaagcgc gctggcgaca gcaacaaaga aaaaatatga acaagagatc    300
```

```
gacgtccgcg tacagatcga tcgcaaaagc ggtgattttg acactttccg tcgctggtta      360
gttgttgatg aagtcaccca gccgaccaag gaaatcaccc ttgaagccgc acgttatgaa      420
gatgaaagcc tgaacctggg cgattacgtt gaagatcaga ttgagtctgt tacctttgac      480
cgtatcacta cccagacggc aaaacaggtt atcgtgcaga aagtgcgtga agccgaacgt      540
gcgatggtgg ttgatcagtt ccgtgaacac gaaggtgaaa tcatcaccgg cgtggtgaaa      600
aaagtaaacc gcgacaacat ctctctggat ctgggcaaca acgctgaagc cgtgatcctg      660
cgcgaagata tgctgccgcg tgaaaacttc cgccctggcg accgcgttcg tggcgtgctc      720
tattccgttc gcccggaagc gcgtggcgcg caactgttcg tcactcgttc caagccggaa      780
atgctgatcg aactgttccg tattgaagtg ccagaaatcg gcgaagaagt gattgaaatt      840
aaagcagcgg ctcgcgatcc gggttctcgt gcgaaaatcg cggtgaaaac caacgataaa      900
cgtatcgatc cggtaggtgc ttgcgtaggt atgcgtggcg cgcgtgttca ggcggtgtct      960
actgaactgg gtggcgagcg tatcgatatc gtcctgtggg atgataaccc ggcgcagttc     1020
gtgattaacg caatggcacc ggcagacgtt gcttctatcg tggtgatga agataaacac      1080 accatggaca tcgccgttga agccggtaat ctggcgcagg cgattggccg taacggtcag     1140
aacgtgcgtc tggcttcgca actgagcggt tgggaactca acgtgatgac cgttgacgac     1200
ctgcaagcta agcatcaggc ggaagcgcac gcagcgatcg acaccttcac caaatatctc     1260
gacatcgacg aagacttcgc gactgttctg gtagaagaag gcttctcgac gctggaagaa     1320
ttggcctatg tgccgatgaa agagctgttg gaaatcgaag gccttgatga gccgaccgtt     1380
gaagcactgc gcgagcgtgc taaaaatgca ctggccacca ttgcacaggc ccaggaagaa     1440
agcctcggtg ataacaaacc ggctgacgat ctgctgaacc ttgaagggt agatcgtgat      1500 ttggcattca aactggccgc ccgtggcgtt tgtacgctgg aagatctcgc cgaacagggc     1560
attgatgatc tggctgatat cgaagggttg accgacgaaa aagccggagc actgattatg     1620
gctgcccgta atatttgctg gttcggtgac gaagcgacta gtggttctgg tcatcaccat     1680
caccatcact ccgcgggtaa agaaaccgct gctgcgaaat ttgaacgcca gcacatggac     1740
tcgccaccgc caactggtct ggtccccgg ggcagcgcgg gttctggtac gattgatgac      1800
gacgacaaga gtccggagct cgtggatccg aattctgtac aggcgcgcct gcaggacgtc     1860
gacggtacca tcgatacgcg ttcgaagctt cggccgcac agctgtatac acgtgcaagc      1920
cagccagaac tcgctcctga agacccagag gatctcgagc accaccacca ccaccactaa     1980
tgttaattaa gttgggcgtt cctaggctga taaaacagaa tttgcctggc ggcagtagcg     2040
cggtggtccc acctgacccc atgccgaact cagaagtgaa acgccgtagc gccgatggta     2100
gtgtggggtc tccc                                                       2114
```

<210> SEQ ID NO 22
<211> LENGTH: 2113
<212> TYPE: DNA
<213> ORGANISM: Artificial Sequence
<220> FEATURE:
<223> OTHER INFORMATION: Synethic construct

<400> SEQUENCE: 22

```
agcaaccgca cctgtggcgc cggtgatgcc ggccacgatg cgtccggcgt agaggatcga       60
gatcgatctc gatcccgcga aattaatacg actcactata ggggaattgt gagcggataa      120
caattcccct ctagaaataa ttttgtttaa ctttaagaag gagatataca tatgaacaaa      180
gaaattttgg ctgtagttga agccgtatcc aatgaaaagg cgctacctcg cgagaagatt      240
```

```
ttcgaagcat tggaaagcgc gctggcgaca gcaacaaaga aaaatatga caagagatc      300 gacgtccgcg tacagatcga tcgcaaaagc ggtgattttg acactttccg tcgctggtta      360
gttgttgatg aagtcaccca gccgaccaag gaaatcaccc ttgaagccgc acgttatgaa      420
gatgaaagcc tgaacctggg cgattacgtt gaagatcaga ttgagtctgt tacctttgac      480
cgtatcacta cccagacggc aaaacaggtt atcgtgcaga agtgcgtga agccgaacgt      540 gcgatggtgg ttgatcagtt ccgtgaacac gaaggtgaaa tcatcaccgg cgtggtgaaa      600
aaagtaaacc gcgacaacat ctctctggat ctgggcaaca cgctgaagc cgtgatcctg      660 cgcgaagata tgctgccgcg tgaaaacttc cgccctggcg accgcgttcg tggcgtgctc      720
tattccgttc gcccggaagc gcgtggcgcg caactgttcg tcactcgttc caagccggaa      780
atgctgatcg aactgttccg tattgaagtg ccagaaatcg cgaagaagt gattgaaatt      840 aaagcagcgg ctcgcgatcc gggttctcgt gcgaaaatcg cggtgaaaac caacgataaa      900
cgtatcgatc cggtaggtgc ttgcgtaggt atgcgtggcg cgcgtgttca ggcggtgtct      960
actgaactgg gtggcgagcg tatcgatatc gtcctgtggg atgataaccc ggcgcagttc     1020
gtgattaacg caatggcacc ggcagacgtt gcttctatcg tggtggatga agataaacac     1080
accatggaca tcgccgttga agccggtaat ctggcgcagg cgattggccg taacggtcag     1140
aacgtgcgtc tggcttcgca actgagcggt tgggaactca acgtgatgac cgttgacgac     1200
ctgcaagcta agcatcaggc ggaagcgcac gcagcgatcg acaccttcac caaatatctc     1260
gacatcgacg aagacttcgc gactgttctg gtagaagaag gcttctcgac gctggaagaa     1320
ttggcctatg tgccgatgaa agagctgttg gaaatcgaag gccttgatga gccgaccgtt     1380
gaagcactgc gcgagcgtgc taaaaatgca ctggccacca ttgcacaggc ccaggaagaa     1440
agcctcggtg ataacaaacc ggctgacgat ctgctgaacc ttgaaggggt agatcgtgat     1500
ttggcattca aactggccgc ccgtggcgtt tgtacgctgg aagatctcgc cgaacagggc     1560
attgatgatc tggctgatat cgaagggttg accgacgaaa aagccggagc actgattatg     1620
gctgcccgta atatttgctg gttcggtgac gaagcgacta gtggttctgg tcatcaccat     1680
caccatcact ccgcgggtaa agaaaccgct gctgcgaaat ttgaacgcca gcacatggac     1740
tcgccaccgc caactggtct ggtccccgg ggcagcgcgg ttctggtac gattgatgac     1800 gacgacaaga gtccgagctc gtggatccga attctgtaca ggcgcgcctg caggacgtcg     1860
acggtaccat cgatacgcgt tcgaagcttg cggccgcaca gctgtataca cgtgcaagcc     1920
agccagaact cgctcctgaa gacccagagg atctcgagcc caccaccac caccactaat     1980 gttaattaag ttgggcgttc ctaggctgat aaaacagaat ttgcctggcg gcagtagcgc     2040
ggtggtccca cctgacccca tgccgaactc agaagtgaaa cgccgtagcg ccgatggtag     2100
tgtggggtct ccc                                                       2113
```

<210> SEQ ID NO 23
<211> LENGTH: 322
<212> TYPE: PRT
<213> ORGANISM: Clostridium perfringens

<400> SEQUENCE: 23

Met Lys Arg Leu Lys Ile Ile Ser Ile Thr Leu Val Leu Thr Ser Val
1               5                   10                  15

Ile Ser Thr Ser Leu Phe Ser Thr Gln Thr Gln Val Phe Ala Ser Glu
            20                  25                  30

```
Leu Asn Asp Ile Asn Lys Ile Glu Leu Lys Asn Leu Ser Gly Glu Ile
            35                  40                  45
Ile Lys Glu Asn Gly Lys Glu Ala Ile Lys Tyr Thr Ser Ser Asp Thr
 50                  55                  60
Ala Ser His Lys Gly Trp Lys Ala Thr Leu Ser Gly Thr Phe Ile Glu
 65                  70                  75                  80
Asp Pro His Ser Asp Lys Lys Thr Ala Leu Leu Asn Leu Glu Gly Phe
                 85                  90                  95
Ile Pro Ser Asp Lys Gln Ile Phe Gly Ser Lys Tyr Tyr Gly Lys Met
            100                 105                 110
Lys Trp Pro Glu Thr Tyr Arg Ile Asn Val Lys Ser Ala Asp Val Asn
        115                 120                 125
Asn Asn Ile Lys Ile Ala Asn Ser Ile Pro Lys Asn Thr Ile Asp Lys
    130                 135                 140
Lys Asp Val Ser Asn Ser Ile Gly Tyr Ser Ile Gly Asn Ile Ser
145                 150                 155                 160
Val Glu Gly Lys Thr Ala Gly Ala Gly Ile Asn Ala Ser Tyr Asn Val
                165                 170                 175
Gln Asn Thr Ile Ser Tyr Glu Gln Pro Asp Phe Arg Thr Ile Gln Arg
            180                 185                 190
Lys Asp Asp Ala Asn Leu Ala Ser Trp Asp Ile Lys Phe Val Glu Thr
        195                 200                 205
Lys Asp Gly Tyr Asn Ile Asp Ser Tyr His Ala Ile Tyr Gly Asn Gln
    210                 215                 220
Leu Phe Met Lys Ser Arg Leu Tyr Asn Asn Gly Asp Lys Asn Phe Thr
225                 230                 235                 240
Asp Asp Arg Asp Leu Ser Thr Leu Ile Ser Gly Gly Phe Ser Pro Asn
                245                 250                 255
Met Ala Leu Ala Leu Thr Ala Pro Lys Asn Ala Lys Glu Ser Val Ile
            260                 265                 270
Ile Val Glu Tyr Gln Arg Phe Asp Asn Asp Tyr Ile Leu Asn Trp Glu
        275                 280                 285
Thr Thr Gln Trp Arg Gly Thr Asn Lys Leu Ser Ser Thr Ser Glu Tyr
    290                 295                 300
Asn Glu Phe Met Phe Lys Ile Asn Trp Gln Asp His Lys Ile Glu Tyr
305                 310                 315                 320
Tyr Leu
```

<210> SEQ ID NO 24
<211> LENGTH: 2533
<212> TYPE: DNA
<213> ORGANISM: Artificial Sequence
<220> FEATURE:
<223> OTHER INFORMATION: Synthetic construct

<400> SEQUENCE: 24

```
atgaacaaag aaattttggc tgtagttgaa gccgtatcca tgaaaaggc gctacctcgc      60 gagaagattt tcgaagcatt ggaaagcgcg ctggcgacag caacaaagaa aaaatatgaa     120
caagagatcg acgtccgcgt acagatcgat cgcaaaagcg gtgattttga cactttccgt     180
cgctggttag ttgttgatga agtcacccag ccgaccaagg aaatcaccct tgaagccgca     240
cgttatgaag atgaaagcct gaacctgggc gattacgttg aagatcagat tgagtctgtt     300
acctttgacc gtatcactac ccagacggca aaacaggtta tcgtgcagaa agtgcgtgaa     360
gccgaacgtg cgatggtggt tgatcagttc cgtgaacacg aaggtgaaat catcaccggc     420
```

```
gtggtgaaaa aagtaaaccg cgacaacatc tctctggatc tgggcaacaa cgctgaagcc      480
gtgatcctgc gcgaagatat gctgccgcgt gaaaacttcc gccctggcga ccgcgttcgt      540
ggcgtgctct attccgttcg cccggaagcg cgtggcgcgc aactgttcgt cactcgttcc      600
aagccggaaa tgctgatcga actgttccgt attgaagtgc cagaaatcgg cgaagaagtg      660
attgaaatta aagcagcggc tcgcgatccg ggttctcgtg cgaaaatcgc ggtgaaaacc      720
aacgataaac gtatcgatcc ggtaggtgct tgcgtaggta tgcgtggcgc gcgtgttcag      780
gcggtgtcta ctgaactggg tggcgagcgt atcgatatcg tcctgtggga tgataacccg      840
gcgcagttcg tgattaacgc aatggcaccg gcagacgttg cttctatcgt ggtggatgaa      900
gataaacaca ccatggacat cgccgttgaa gccggtaatc tggcgcaggc gattggccgt      960
aacggtcaga acgtgcgtct ggcttcgcaa ctgagcggtt gggaactcaa cgtgatgacc     1020
gttgacgacc tgcaagctaa gcatcaggcg gaagcgcacg cagcgatcga caccttcacc     1080
aaatatctcg acatcgacga agacttcgcg actgttctgg tagaagaagg cttctcgacg     1140
ctggaagaat tggcctatgt gccgatgaaa gagctgttgg aaatcgaagg ccttgatgag     1200
ccgaccgttg aagcactgcg cgagcgtgct aaaaatgcac tggccaccat tgcacaggcc     1260
caggaagaaa gcctcggtga taacaaaccg gctgacgatc tgctgaacct tgaaggggta     1320
gatcgtgatt tggcattcaa actggccgcc cgtggcgttt gtacgctgga agatctcgcc     1380
gaacagggca ttgatgatct ggctgatatc gaagggttga ccgacgaaaa agccggagca     1440
ctgattatgg ctgcccgtaa tatttgctgg ttcggtgacg aagcgactag gccggggcag     1500
cgcgggttct ggtacgattg atgacgacga caagagtccg ggagctcgtg gatccgaatt     1560
cagtgaatta ggcaatacta agaaaataga gctgaaaaat caaatggag aataataaa     1620
agaagatgga aaggaagcta ttaaatacac ttctattgat acttcttcat gtaaagggtt     1680
aaaagcaaca ttaagtggaa cttttgttga agatcaatat tctgataaga aaactgcttt     1740
actaaattta gatgggttta taccttcagg taagaaagta tctggttcta catattatgg     1800
aaagatgaag tggcctgaag tttatagaat tagtatagaa agcgctgata cagctaataa     1860
agtaaaaata gcaaattcta tacctaaaaa tactatagat aaaaaggagg tatctaattc     1920
aattggatat tcaattggag gaaatatatc tgttgaaggt aaaagtggta gtgcaggaat     1980
aaatgcttca tacagtgtac aaaatactat aagctatgaa caacctgatt ttagaacaat     2040
ccaaagaaaa gatgaagaaa agttagcttc atgggatata aaatttgttg aaactaaaga     2100
tggttataat ctggattcat atcatggtat ttatgggaat caattattta tgaaatcaag     2160
attatataat aatggttatg aaaactttac tgatgataga gatctctcaa ctttaatttc     2220
aggtggcttt tcacctaata tggcagtagc tttaacagcg ccaaaagatg ctaaagaatc     2280
tatgataaca gttacatata aaagatttga cgatgagtat actttgaatt gggaaactac     2340
tcaatggagg ggatcaaata aacgttcaac tgcatgtgaa tatactgaat ttatgtttaa     2400
aattaattgg gaaaaccata caattgaacg ttttctaaag cttgcggccg cacagctgta     2460
tacacgtgca agccagccag aactcgctcc tgaagaccca gaggatctcg agcaccacca     2520
ccaccaccac taa                                                        2533
```